(12) United States Patent
McCaig

(10) Patent No.: US 8,536,404 B2
(45) Date of Patent: Sep. 17, 2013

(54) PLANT ROOT-SPECIFIC NEMATODE RESISTANCE

(75) Inventor: Bonnie McCaig, Durham, NC (US)

(73) Assignee: BASF Plant Science GmbH (DE)

( * ) Notice: Subject to any disclaimer, the term of this patent is extended or adjusted under 35 U.S.C. 154(b) by 49 days.

(21) Appl. No.: 13/133,391

(22) PCT Filed: Nov. 30, 2009

(86) PCT No.: PCT/EP2009/066062
§ 371 (c)(1),
(2), (4) Date: Jun. 8, 2011

(87) PCT Pub. No.: WO2010/066600
PCT Pub. Date: Jun. 17, 2010

(65) Prior Publication Data
US 2011/0247096 A1    Oct. 6, 2011

Related U.S. Application Data

(60) Provisional application No. 61/201,471, filed on Dec. 11, 2008.

(51) Int. Cl.
*C12N 15/87* (2006.01)
*C12N 15/00* (2006.01)
*C12N 15/82* (2006.01)
*A01H 5/10* (2006.01)
*C07H 21/04* (2006.01)

(52) U.S. Cl.
USPC ........... 800/279; 800/278; 800/287; 800/295; 800/301; 435/320.1; 536/24.1; 536/23.6

(58) Field of Classification Search
None
See application file for complete search history.

(56) References Cited

U.S. PATENT DOCUMENTS

| 7,396,979 B2 | 7/2008 | Alexandrov |
|---|---|---|
| 2004/0019927 A1 | 1/2004 | Sherman |
| 2006/0057724 A1 * | 3/2006 | Alexandrov et al. ......... 435/419 |

FOREIGN PATENT DOCUMENTS

| WO | WO 03/066865 | 8/2003 |
|---|---|---|
| WO | WO03066865 A2 * | 8/2003 |

OTHER PUBLICATIONS

KWS SAAT AG. 2003. New Nucleic acid for specific regulation of gene expression in plant tissues affected by pathogens, useful for making nematode resistant transgenic plants. Synopsis and translation of WO2003066865. 3 pages.*
Uniprot. 2008. Accession B3TPR9.*
Pennycooke Joyce C et al: "The low temperature-responsive, Solanum CBF1 genes maintain high identity in their upstream regions in a genomic environment undergoing gene duplications, deletions, and rearrangements" Plant Molecular Biology vol. 67, No. 5, Jul. 2008, pp. 483-497, the whole document, XP002568204.
Database UniProt [online] Sep. 2, 2008, "SubName: Full=CBF3 protein;" XP002568205.
Durrant Wendy E et al: "cDNA-AFLP reveals a strinking overlap in race-specific resistance and wound response gene expression profiles" Plant Cell, vol. 12, No. 6, Jun. 2000, pp. 963-977, XP002568206, the whole document.
Rowland Owen et al: "Functional analysis of Avr9/Cf-9 rapidly elicited genes identifies a protein kinase, ACIK1, that is essential for full Cf-9-dependent disease resistance in tomato" Plant Cell, vol. 17, No. 1, Jan. 2005, pp. 295-310, xp002568207, the whole document.
Zhu Jin-Wen et al: "Transcript profiling for Avr4/Cf-4- and Avr9/Cf-9-dependent defence gene expression" European Journal of Plant Pathology, vol. 122, No. 2, Oct. 2008, pp. 307-314, XP002568208, the whole document.
Liu Qiang et al: "Two transcription factors, DREB1 and DREB2, with an EREBP/AP2 DNA binding domain separate two cellular signal transduction pathways in drought-and low-temperature-responsive gene expression, respectively, in Arabidopsis" Plant Cell, American Society of Plant Physiologists, Rockville, MD, US., vol. 10, No. 8, Aug. 1, 1998, pp. 1391-1406, XP002145075.
Goddijn O J M et al: "Differential Gene Expression in Nematode-Induced Feeding Sturctures of Trnasgenic Palnts Harbouring Promoter-Gusa Fusion Constructs" Plant Journal, Blackwell Scientific Publications, Oxford, GB, vol. 4, No. 5, Jan. 1, 1993, pp. 863-873, XP0020000605, the whole document.

* cited by examiner

*Primary Examiner* — Cathy Kingdon Worley
*Assistant Examiner* — Jeffrey Bolland
(74) *Attorney, Agent, or Firm* — Patricia A. McDaniels

(57) ABSTRACT

The invention provides expression vectors comprising root-specific promoters in operative association with polynucleotides that are down-regulated in syncytia of nematode-infected plants, for use in methods of producing transgenic plants with increased resistance to nematode infestation. The invention also provides nematode-resistant transgenic plants and seeds comprising such expression vectors.

4 Claims, 7 Drawing Sheets

Figure 1a

| Gene or promoter name | Species | SEQ ID NO: |
|---|---|---|
| GmSerine-Arginine-rich DNA | Glycine max | 1 |
| GmSerine-Arginine-rich Protein | Glycine max | 2 |
| TA52573_3847 DNA | Glycine max | 3 |
| TA52573_3847 Protein | Glycine max | 4 |
| TA52574_3847 DNA | Glycine max | 5 |
| TA52574_3847 Protein | Glycine max | 6 |
| SRrich Gsoja DNA | synthetic | 7 |
| SRrich Gsoja Protein | synthetic | 8 |
| TA12732_47664 DNA | P. tremula x P. tremuloides | 9 |
| TA12732_47664 Protein | P. tremula x P. tremuloides | 10 |
| TA15414_3694 DNA | Populus trichocarpa | 11 |
| TA15414_3694 Protein | Populus trichocarpa | 12 |
| TA28460_3708 DNA | Brassica napus | 13 |
| TA28460_3708 Protein | Brassica napus | 14 |
| CAC03604_At DNA | Arabidopsis thaliana | 15 |
| CAC03604_At Protein | Arabidopsis thaliana | 16 |
| TA24252_4113 DNA | Solanum tuberosum | 17 |
| TA24252_4113 Protein | Solanum tuberosum | 18 |
| TA26184_4113 DNA | Solanum tuberosum | 19 |
| TA26184_4113 Protein | Solanum tuberosum | 20 |
| TA39514_4081 DNA | Solanum lycopersicon | 21 |
| TA39514_4081 Protein | Solanum lycopersicon | 22 |
| TA8600_4100 DNA | Nicotiana benthamiana | 23 |
| TA8600_4100 Protein | Nicotiana benthamiana | 24 |
| TA15942_4097 DNA | Nicotiana tabacum | 25 |
| TA15942_4097 Protein | Nicotiana tabacum | 26 |

Figure 1b/4

| TA23961_3880 DNA | Medicago truncatula | 27 |
|---|---|---|
| TA23961_3880 Protein | Medicago truncatula | 28 |
| AAG51556_At DNA | Arabidopsis thaliana | 29 |
| AAG51556_At Protein | Arabidopsis thaliana | 30 |
| AAK93651_At DNA | Arabidopsis thaliana | 31 |
| AAK93651_At Protein | Arabidopsis thaliana | 32 |
| ABF96206_Os DNA | Oryza sativa | 33 |
| ABF96206_Os Protein | Oryza sativa | 34 |
| TA44013_29760 DNA | Vitis vinifera | 35 |
| TA44013_29760 Protein | Vitis vinifera | 36 |
| AVR9-elicited_111B DNA | Glycine max | 37 |
| AVR9-elicited_111B Protein | Glycine max | 38 |
| GmbHLH_47172355 DNA | Glycine max | 39 |
| GmbHLH_47172355 Protein | Glycine max | 40 |
| TA11822_34305 DNA | Lotus japonicus | 41 |
| TA11822_34305 Protein | Lotus japonicus | 42 |
| FF401851_Vigna DNA | Vigna unguiculata | 43 |
| FF401851_Vigna Protein | Vigna unguiculata | 44 |
| bHLH_Phaseolus DNA | synthetic | 45 |
| bHLH_Phaseolus Protein | synthetic | 46 |
| EV256603_Medicago DNA | Medicago truncatula | 47 |
| EV256603_Medicago Protein | Medicago truncatula | 48 |
| GmDirigent_59580836 DNA | Glycine max | 49 |
| GmDirigent_59580836 Protein | Glycine max | 50 |
| TA50990_3847 DNA | Glycine max | 51 |
| TA50990_3847 Protein | Glycine max | 52 |
| FF399867_Vu DNA | Vigna unguiculata | 53 |
| FF399867_Vu Protein | Vigna unguiculata | 54 |
| dirigent_Phaseolus DNA | synthetic | 55 |
| dirigent_Phaseolus Protein | synthetic | 56 |
| TPP-like promoter | Arabidopsis thaliana | 57 |
| MtN3-like promoter | Glycine max | 58 |
| At5g12170 promoter | Arabidopsis thaliana | 59 |
| PcUbi4-2 promoter | Petroselinum crispum | 60 |

Figure 2a

```
SEQ ID NO:2   (1)  -MRGR--SYSPSPPPPRYSRRGGGRSPSPRG-RYPPRP---RQQDLPTSL
SEQ ID NO:6   (1)  -MRGR--SYSPSPPPPRYSRRGGGRSPSPRG-RYPPRP---RQQDLPTSL
SEQ ID NO:4   (1)  -MRGR--SYSPSPPPRHSRRGGGGRSPSPRG-RYPPRP---RQQDLPTSL
SEQ ID NO:8   (1)  -MRGR--SYSPSPPPPRYSRRGGGRSPSPRG-RYPPRP---RQQDLPTSL
SEQ ID NO:10  (1)  -MRGR--SYSPSPPRGY-SRR--GRSPSPRG-RYGG-----RSRDLPTSL
SEQ ID NO:12  (1)  -MRGR--SYSPSPPRGY-SRR--GRSPSPRG-RYGG-----RSRDLPTSL
SEQ ID NO:14  (1)  -MRGR--SYTPSPPRGY-GRR--GRSPSPRG-RYGG----GRDRDLPTSL
SEQ ID NO:16  (1)  -MRGR--SYTPSPPRGY-GRR--GRSPSPRG-RFGGS----RDSDLPTSL
SEQ ID NO:18  (1)  -MRGR--SYSPSPPRGY-GRR--GRSPSPRGGRYGG-----RSRDDPTTL
SEQ ID NO:20  (1)  -MRRR--SYSPSPQRGY-GRR--GRSPSPRG-RYGG-----HSRDGPTSL
SEQ ID NO:22  (1)  -MRRR--SYSPSPPRGY-GRR--GRSPSPRG-RYAG-----HGRDGPTSL
SEQ ID NO:24  (1)  -MRRR--SYSPSPPRGY-GSRG-GRSPSPRG-RYGG-----RSRDAPTSL
SEQ ID NO:26  (1)  -MRRR--SYSPSPPRGY-GRRG-GRSPSPRG-RYGG-----RSRDAPTSL
SEQ ID NO:36  (1)  -MRGR--SYSPSPPRAY-GRR--GRSPSPRG-RYGGR---GSARDLPTSL
SEQ ID NO:28  (1)  -MRGRSYSYSPSPPRRYGGRR---RSPSPRG-RYGGRYGGRDRDLPTSL
SEQ ID NO:30  (1)  -MRGR--SYTPSPPRGY-GRR--GRSPSPRG-RYGG-----RSRDLPTSL
SEQ ID NO:32  (1)  -MRGR--SYTPSPPRGY-GRR--GRSPSPRG-RYGG-----RSRDLPTSL
SEQ ID NO:34  (1)  MGRGY--DYGPSPPREY-RRR--ARSPSPRG-RYGG-----RDRDLPTSL

SEQ ID NO:2   (44) LVRNLRHDCRPEDLRRPFGQFGPLKDIYLPKDYYTGEPRGFGFVQFVDPA
SEQ ID NO:6   (44) LVRNLRHDCRPEDLRIPFGQFGPLKDIYLPKDYYTGEPRGFGFVQFVDPA
SEQ ID NO:4   (44) LVRNLRHDCRPEDLRRPFGQFGPLKDIYLPKDYYTGEPRGFGFVQYVDPA
SEQ ID NO:8   (15) LVRNLRHDCRPEDLRRPFGQFGPLKDIYLPKDYYTGEPRGFGFVQYVDPA
SEQ ID NO:10  (39) LVRNLRHDCRPEDLRRPFEQFGALKDIYLPRDYYTGEPRGFGFVQYADPH
SEQ ID NO:12  (39) LVRNLRHDCRPEDLRRPFEQFGALKDIYLPRDYYTGEPRGFGFVQYADPH
SEQ ID NO:14  (40) LVRNLRHDCRQEDLRRPFEQFGPVKDIYLPRDYYTGDPRGFGFIQYVDPA
SEQ ID NO:16  (40) LVRNLRHDCRQEDLRRPFEQFGPVKDIYLPRDYYTGDPRGFGFIQFMDPA
SEQ ID NO:18  (40) LVRNLRHDCRPEDLKKPFGQIGPVKDIYLPRDYYTREPRGFGFIQYLDPA
SEQ ID NO:20  (39) LVRNLRHDCRPEDLRRPFGQFGPVKDIYLPKDYYTGEPRGFGFVQFVDPA
SEQ ID NO:22  (39) LVRNLRHDCRPEDLRRPFGQFGPVKDIYLPKDYYTGEPRGFGFVQFVDPA
SEQ ID NO:24  (40) LVRNLRHDCRPEDLRRPFGQFGPVKDIYLPRDYYGQPRGFGFVQFVDPA
SEQ ID NO:26  (40) LVRNLRHDCRPEDLRRPFGQFGPVKDIYLPRDYYGQPRGFGFVQFVDPA
SEQ ID NO:36  (41) LVRNLRHDCRGEDLRRPFGQFGPLKDIYLPRDYYTGEPRGFGFVQYVDPA
SEQ ID NO:28  (46) LVRNLAKDCRPEDLHDPFGQFGPVKDVYLPRDYYTGEPRGFGFVQFVDPA
SEQ ID NO:30  (39) LVRNLRHDCRQEDLRKSFEQFGPVKDIYLPRDYYTGDPRGFGFVQFMDPA
SEQ ID NO:32  (39) LVRNLRHDCRQEDLRKSFEQFGPVKDIYLPRDYYTGDPRGFGFVQFMDPA
SEQ ID NO:34  (40) LVRNLRRDCRPDDLRRPFGKFGRVKDIYLPRDYYTGEPRGFGFIQYYDPE

SEQ ID NO:2   (94) DAADAKYHMDGQVLLGRELTVVFAEENRKKPTEMRTRER-----RGRFSD
SEQ ID NO:6   (94) DAADAKYHMDGQVLLGRELTVVFAEENRKKPTEMRTRER-----RGRFSD
SEQ ID NO:4   (94) DAADAKYHMDGQVLLGRELTVVFAEENRKKPTEMRTRER-----RGRFYD
SEQ ID NO:8   (65) DAADAKYHMDGQVLLGRELTVVFAEENRKKPTEMRTRER-----RGRFYD
SEQ ID NO:10  (89) DAAEAKHHMDGRVFLGRELTVVFAEENRKKPVDMRARERTAT--RGRVGD
SEQ ID NO:12  (89) DAAEAKHHMDGRVFLGRELTVVFAEENRKKPVDMRARERTAT--RGRVGD
SEQ ID NO:14  (90) DAAEAKHHMEGYLLLGRELTVVFAEENRKKPTEMRTRDRGGR--SNRFND
SEQ ID NO:16  (90) DAAEAKHQMDGYLLLGRELTVVFAEENRKKPTEMRTRDRGGR--SNRFQD
SEQ ID NO:18  (90) DAAEAKYQMDGQAFQGRQLTVVFAEENRKKPQEMRARER-GSGRGGRNYD
SEQ ID NO:20  (89) DAADAKYQMDGQGFQGRQLTVVFAEENRKKPTEMRSRERSGSHRSSRSHD
SEQ ID NO:22  (89) DAADAKYQMDGQGFQGRQLTVVFAEENRKKPTEMRSRERSGSHRSSRSYD
SEQ ID NO:24  (90) DAAEAKYQMDGQGFQGRQLTVVFAEENRKKPTEMRARERSGSGRS-RSYD
SEQ ID NO:26  (90) DAAEAKYQMDGQGFQGRQLTVVFAEENRKKPTEMRARERSGSGRS-RSYD
SEQ ID NO:36  (91) DAAEAKYQMDGQILHGRELTVVFAEENRKKPSDMRARERG----RGRFYD
SEQ ID NO:28  (96) DAADAKYHMDGQVLLGRELTVVFAEENRKKPQEMRARER------GRSYD
SEQ ID NO:30  (89) DAADAKHHMDGYLLLGRELTVVFAEENRKKPTEMRARERGG----GRFRD
SEQ ID NO:32  (89) DAADAKHHMDGYLLLGRELTVVFAEENRKKPTEMRARERGG----GRFRD
SEQ ID NO:34  (90) DAADAKYHMDGQILLGREVTVVFAEENRKKPSEMRARERVGS--RDRSYD
```

Figure 2b

```
SEQ ID NO:2  (139) RRRSPPRY-SRS--PRYSRSPRYSRSPPPRHRSRSHSRDYYSP--KRREY
SEQ ID NO:6  (139) RRRSPPRY-SRS--PRYSRSPPP------RHRSRSHSRDYYSP--KRREY
SEQ ID NO:4  (139) RRRSPPRY-SRS--PRYSRSPPP------RHRSRSRSRDYYSPPAKRREY
SEQ ID NO:8  (110) RRRSPPRY-SRS--PRYSRSPPP------RHRSRSRSRDYYSPPAKRREY
SEQ ID NO:10 (137) RRRSPPRY-SRS--PRHSRSPPP-----RHATSRSHSRDFYSPP-KRRHH
SEQ ID NO:12 (137) RRRSPPRY-SRS--PRHSRSPPP-----RHATSRSHSRDYYSPP-KRRHP
SEQ ID NO:14 (138) RRRSPPRY-SRSPPP------------RRGGRTSRSRE-YNSPPPKRHQ
SEQ ID NO:16 (138) RRRSPPRY-SRSPP-------------RRGRRSRSRSCGYNSPP-AKRHQ
SEQ ID NO:18 (139) RRGTPPRY-HNSP--RYSRSPPP-----------RGRDYYSPP-KRRQY
SEQ ID NO:20 (139) RRRTPP---SR-----YARAGS-------------HSRD-YSP--KRRQY
SEQ ID NO:22 (139) RRRTPP---SR-----YARPG--------------SHSRD-YSP--KRRPY
SEQ ID NO:24 (139) RRRYSPQY-SRSPPPRYARSPS-----------RSHG---YSP--KRRQY
SEQ ID NO:26 (139) RRRYSPQY-SRSPPPRYARS--------------RSRG-YSP--KRRQY
SEQ ID NO:36 (137) RRRSPLRY-SRSPPPRHARSP------------SRGRDYYSPSPKRRQY
SEQ ID NO:28 (140) YRRSPRRR-SRS--PRYARTY------------SRSPDYTPSP-RPRRY
SEQ ID NO:30 (135) RRRTPPRYYSRS------RSPPP----RRGR-SRSRSGDYYSPP-PRRHH
SEQ ID NO:32 (135) RRRTPPRYYSRS------RSPPP----RRGR-SRSRSGDYYSPP-PRRHH
SEQ ID NO:34 (138) RRSRSPRY-SRS------RSP------VYSPRSRSRSR-SYSPAPKRKHY

SEQ ID NO:2  (184) SRSVSPEGRRYSRERSYSQHNRERSFS----------RSPPYNGG-----
SEQ ID NO:6  (178) SRSVSPEGRRYSRERSYSQHNRERSYS----------RSPPYNGG-----
SEQ ID NO:4  (180) SRSVSPEDRRYSRERSFSQHSRERSYS----------RSPPYNGG-----
SEQ ID NO:8  (151) SRSVSPEDRRYSRERSFSQHSRERSYS----------RSPPYNGG-----
SEQ ID NO:10 (178) SRSVSPRERRYSQE---------RSYS----------RSRSHSQTP----
SEQ ID NO:12 (178) SRSVSPRERRYSQE---------RSYS----------RSRSHSQTP----
SEQ ID NO:14 (174) SRSVSPQERRYEKE---------RSYS----------RSPPRNG------
SEQ ID NO:16 (173) SRSVSPDRRYEKE---------RSYS----------RSPPHNG------
SEQ ID NO:18 (173) SRSVSPEEKRYSRE---------RSYSPRGGQGRAYSQSPPREQSPP-FN
SEQ ID NO:20 (165) SRSVSPEEKRYSRE---------RSYS----------RSPPRGLSPPPHN
SEQ ID NO:22 (165) SRSVSPEEKRYSRE---------RSYS----------RSPPRDLSPPPHN
SEQ ID NO:24 (172) SRSVSPEEKRYSRE---------RSYS----------RSPARDISPP-YN
SEQ ID NO:26 (170) SRSVSPEEKRYSRE---------RSYS----------RSPARDISPP-YN
SEQ ID NO:36 (173) SRSVSPQDRRYSRDRSYTPDGRRRSYT----------RSPPYNG------
SEQ ID NO:28 (173) SRSISPRDERYRR----------RSYS----------RSP--------YR
SEQ ID NO:30 (173) PRSISPREERYDG---------RRSYS----------RSPASDG------
SEQ ID NO:32 (173) PRSISPREERYDG---------RRSYS----------RSPASDG------
SEQ ID NO:34 (174) S-SRSPARR------------ERSLS----------RSPADSR------

SEQ ID NO:2  (219) -SRSRSQSPAKG---------PG--RSRSPSLNRDEREPARGRSPSQ---
SEQ ID NO:6  (213) -SRSRSQSPAKG---------PV--RSRSPSLNRDEREPARGRSPSQ---
SEQ ID NO:4  (215) -SRSRSQSPAKG---------PG--QSRSPSPNRDGREPARGRSPSQ---
SEQ ID NO:8  (186) -SRSRSQSPAKG---------PG--QSRSPSPNRDGREPARGRSPSQ---
SEQ ID NO:10 (205) -NRGQIRSPARSPARS-RSRSPRRSRSRSPIHDEYPKEVNGDKSPSP---
SEQ ID NO:12 (205) -NRGQIRSPVRS-----RSSSPRKSRSRSPIHDEYPKEVNGDKSPSP---
SEQ ID NO:14 (199) -SRARSGSHEKAKKSYSGSRSPRRSVSPRRDRATLLNKPG-AWS------
SEQ ID NO:16 (198) -SRVRSGSPGRVKSHS---RSPRRSVSPRKNRSYTPEQAR-SQSPVPRQS
SEQ ID NO:18 (213) GSRSRSQSPVREHSPP---YNGSRSRSRSPVR-ARSPVRGHSRRLSPSQG
SEQ ID NO:20 (196) GSRSRSQTPVRERPPY---NGSPRSRSRSPVRRERSPVRGHSR--SPSRS
SEQ ID NO:22 (196) GSRSRSQTPVREHPPY---NGSPRSRSRSPVRRERSPVRGHSR--SPSRS
SEQ ID NO:24 (202) GSRSRSQTPVRKHSPY---DDGRRSRSRSPVK-ERFAVRVHSR--SPSRS
SEQ ID NO:26 (200) GSRSRSQTPVREHSPY---DDGRRSRSRSPVK-ERSPVRGHSR--SPSRS
SEQ ID NO:36 (207) -SRSRSQSPIRG-------ESPSRLQSRSPDPEDYPREAVRDRSPSE---
SEQ ID NO:28 (195) SPYG---------------------SRSPDR-GRSYSRSISR--SPGYS
SEQ ID NO:30 (198) -SRGRSLTPVRGKSRS-LTPALEEA-------------------------
SEQ ID NO:32 (198) -SRGRSLTPVRGKSRS-LSPSPRRSISRSPRRSRSPRRSRRSYTPEPARS
SEQ ID NO:34 (194) -SRSRSLSDDRR--------------SKSPDRERSLSVSR----------
```

Figure 2c

```
SEQ ID NO:2   (254) --------------------
SEQ ID NO:6   (248) --------------------
SEQ ID NO:4   (250) --------------------
SEQ ID NO:8   (220) --------------------
SEQ ID NO:10  (250) --------------------
SEQ ID NO:12  (246) --------------------
SEQ ID NO:14  (241) --------------------
SEQ ID NO:16  (243) RSPTPVPRGAQNGDRSPSQ---
SEQ ID NO:18  (259) HSRSPDAVHYSRNPDHDVSPRH
SEQ ID NO:20  (241) ----PGCAPYSP----------
SEQ ID NO:22  (241) RSRSPGCAPYSP----------
SEQ ID NO:24  (246) RS--PGDVHYSRDPDHDVSPRH
SEQ ID NO:26  (244) RS--PGDVRYSRDPDHDVSPRH
SEQ ID NO:36  (246) --------------------
SEQ ID NO:28  (220) R-------------------
SEQ ID NO:30  (221) --------------------
SEQ ID NO:32  (246) RSQSPHG-GQYDEDRSPSQ---
SEQ ID NO:34  (219) --------------------
```

Figure 3

```
SEQ ID NO:40    (1)   MDMNSSGGACGWLYDYGFDIP--VAGSDFMASDSG---GFSWGPQ-----
SEQ ID NO:42    (1)   MEIDSSGDSC-WLYDYGFDDISVAAAADFMVADSA---DFTWVP------
SEQ ID NO:48    (1)   MDMDSTGGSSIWLYDYGYDDISISAADFMASDSSAAASTFTWMPQPQSQT
SEQ ID NO:46    (1)   MDMNSSSGASGWLYDYGFDIPVAGADFMAAADSG----GFSWGPQ-----
SEQ ID NO:44    (1)   MDMNSSSGASGWLYDYGFDIPVAGADFMVAADSG----GFSWGPQ-----

SEQ ID NO:40   (41)   ------------------SYN-FKGPSNMSLEMEYSLDSTVMENGPSKRL
SEQ ID NO:42   (41)   -------------------------SNMNLEMEYSLDSTVFESGPSKRL
SEQ ID NO:48   (51)   QIINPPSSHMSLEMDYSLDSTVMESNPSKRMEMEYSLDSTVLENGPSKRL
SEQ ID NO:46   (27)   ------------------NHTLKAPSNTSLDMEYSLDSTVLENGPSKRL
SEQ ID NO:44   (42)   ------------------NHTLKGPSHTSLEMEYSLDSTVLENSPSKRL

SEQ ID NO:40   (72)   RTESCASGSKACREKLRRDKLNERFLELSSILEPGRQPKTDKVALLSDAA
SEQ ID NO:42   (65)   RTESSVSGSKACREKLRRDKLNERFLELSSILEPGRQPKTDKAAIISDAV
SEQ ID NO:48  (101)   RTESYASSSKAGREKVRRDKLNDRFMELSSVLEPDTLPKTDKVSLLNDAV
SEQ ID NO:46   (58)   RTESCASGAKACREKLRRDKLNERFLELSSILEPGRPPKTDKVVILSDAV
SEQ ID NO:44   (73)   RTESCASGAKACREKMRRDKLNDRFLELSSILEPGRPPKTDKVAILSDAA

SEQ ID NO:40  (122)   RVVIQLRNEAERLKEMNDELQAKVKELKGEKNELRDEKNRLKEEKEKLEK
SEQ ID NO:42  (115)   RVVTQLRNEAEKLKEMNNDLQEKIKELKAEKNEIRDEKNKLKLDKEKLEK
SEQ ID NO:48  (151)   RVVTQLRNEAERLKERNDELREKVKELKAEKKELRDEKNKLKLDKEKLEQ
SEQ ID NO:46  (108)   RAVVQLRNEAERLKEMNDELQGKVKELKAEKNELRDEKNMLKEEKEKLEQ
SEQ ID NO:44  (123)   RVVVQLRNETERLKEMNDELQGKVKELKAEKNELRDEKNMLKDEKEKLEQ

SEQ ID NO:40  (172)   QVKLTNI-QPSFLPQAPDAKGQ--VGSHKLIPFIGYPGIAMWQFMSPAAV
SEQ ID NO:42  (165)   KVKLRNV-QPGFLPHADAVKGKGAASHKLIPYIGYPGIAMWQFMPSAVL
SEQ ID NO:48  (201)   QVKLASV-QSNFLSNAMAAKGQ--TANHKLMPFIGYPGISMWQFMSPATV
SEQ ID NO:46  (158)   QVKLTNVMRHSFLPQAPAAKEQ--VGSHKLIPFIGYPGIAMWQFMPPAAV
SEQ ID NO:44  (173)   QVKLTNI-HNSFVPQAQAAKGQ--VGSHKLIPFIGYPGIAMWQFMPPAAV

SEQ ID NO:40  (219)   DTSKDHLLRPPVA
SEQ ID NO:42  (214)   DTSRDHLLRPPVA
SEQ ID NO:48  (248)   DTSQDHLLRPPVA
SEQ ID NO:46  (206)   DTSKDHLLRPPVA
SEQ ID NO:44  (220)   DTSKDHLLRPPVA
```

Figure 4

```
SEQ ID NO:50    (1)    MGTKLFHTLLLLSYALSNVIGEETGFVGTLHPKSLGLHKKQTLSHFKFYW
SEQ ID NO:52    (1)    MSTKLLLTLILISYTLSNVIGEETGFVGTLHPKSLGLHKKQTLSHFKFYW
SEQ ID NO:56    (1)    MATQLLLTLFLLSFTLTTIKAEDTGFVGTVDPKSLGLNKKQTLSHFRFYW
SEQ ID NO:54    (1)    MATQLLLTLFLLSFTVATIQAEDTGYVGTVDPKSLGLNKKKTLSHFRLYW

SEQ ID NO:50    (51)   HDIVSSGANSTSATVIPPLPKYNTSTSFGMVNVMDNPLTLGPEMGSKLVG
SEQ ID NO:52    (51)   HDIVSSGANSTSATIIPPLPKYNTTTSFGMVNVMDNPLTLGPELGSKLVG
SEQ ID NO:56    (33)   HDIIS-GSNATAVEIIEPLPKYNTTTSFGSVTVTDNALTLGPELSSKVVG
SEQ ID NO:54    (51)   QDVIS-GSNATAINIIPAIPKYNTTTSFGSVTVTDNALTVGPELSSKVVG

SEQ ID NO:50    (101)  RAEGFYALTSQSQINLLMVMNFALFEGKYNGSTITIVGRNAVSENEKDIP
SEQ ID NO:52    (101)  RAEGFYALTSQSQINLLMVMNFALFEGKYNGSTITIVGRNAVSENEKDIP
SEQ ID NO:56    (82)   RSEGIYALTSQSQVTLLMVMNFVLSEGKYNGSAITIVGRNVAYEEAKELP
SEQ ID NO:54    (100)  RSEGIYALTSQSQVTLLMVMNFVLTEGKYNGSSLTIVGRNVAYDEQKELP

SEQ ID NO:50    (151)  VVGGSGIFKFAKGYAHAKTYFFDPKTGDATTEYNVYVLHNE
SEQ ID NO:52    (151)  VVGGSGVFKFAKGYAHAKTYFFDPKTGDATTEYNIYVLHYE
SEQ ID NO:56    (132)  VIGGSGVFKFATGYAKAKTYYFDPKTGDATTEYNIYVFHY-
SEQ ID NO:54    (150)  VVGGSGVFKFATGYAHAKTYHFDPTTGDATTEYNIYVFHY-
```

PLANT ROOT-SPECIFIC NEMATODE RESISTANCE

This application is a national stage application under 35 U.S.C. §371 of PCT/EP2009/066062, filed Nov. 30, 2009, which claims the priority benefit of U.S. provisional patent application Ser. No. 61/201,471, filed Dec. 11, 2008. The entire contents of each of the above-identified applications are incorporated herein by reference.

FIELD OF THE INVENTION

The invention relates to enhancement of agricultural productivity through use of nematode-resistant transgenic plants and seeds, and methods of making such plants and seeds.

BACKGROUND OF THE INVENTION

Nematodes are microscopic roundworms that feed on the roots, leaves and stems of more than 2,000 row crops, vegetables, fruits, and ornamental plants, causing an estimated $100 billion crop loss worldwide. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore parasitic on a large number of crop species. The cyst- and lesion-forming nematode species have a more limited host range, but still cause considerable losses in susceptible crops.

Parasitic nematodes are present throughout the United States, with the greatest concentrations occurring in the warm, humid regions of the South and West and in sandy soils. Soybean cyst nematode (Heterodera glycines), the most serious pest of soybean plants, was first discovered in the United States in North Carolina in 1954. Some areas are so heavily infested by soybean cyst nematode (SCN) that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. Nematode infestation, however, can cause significant yield losses without any obvious above-ground disease symptoms. The primary causes of yield reduction are due to underground root damage. Roots infected by SCN are dwarfed or stunted. Nematode infestation also can decrease the number of nitrogen-fixing nodules on the roots, and may make the roots more susceptible to attacks by other soil-borne plant nematodes.

The nematode life cycle has three major stages: egg, juvenile, and adult. The life cycle varies between species of nematodes. The life cycle of SCN is similar to the life cycles of other plant parasitic nematodes. The SCN life cycle can usually be completed in 24 to 30 days under optimum conditions, whereas other species can take as long as a year, or longer, to complete the life cycle. When temperature and moisture levels become favorable in the spring, worm-shaped juveniles hatch from eggs in the soil. Only nematodes in the juvenile developmental stage are capable of infecting soybean roots.

After penetrating soybean roots, SCN juveniles move through the root until they contact vascular tissue, at which time they stop migrating and begin to feed. With a stylet, the nematode injects secretions that modify certain root cells and transform them into specialized feeding sites. The root cells are morphologically transformed into large multinucleate syncytia (or giant cells in the case of RKN), which are used as a source of nutrients for the nematodes. The actively feeding nematodes thus steal essential nutrients from the plant resulting in yield loss. As female nematodes feed, they swell and eventually become so large that their bodies break through the root tissue and are exposed on the surface of the root.

After a period of feeding, male SCN migrate out of the root into the soil and fertilize the enlarged adult females. The males then die, while the females remain attached to the root system and continue to feed. The eggs in the swollen females begin developing, initially in a mass or egg sac outside the body, and then later within the nematode body cavity. Eventually the entire adult female body cavity is filled with eggs, and the nematode dies. It is the egg-filled body of the dead female that is referred to as the cyst. Cysts eventually dislodge and are found free in the soil. The walls of the cyst become very tough, providing excellent protection for the approximately 200 to 400 eggs contained within. SCN eggs survive within the cyst until proper hatching conditions occur. Although many of the eggs may hatch within the first year, many also will survive within the protective cysts for several years.

A nematode can move through the soil only a few inches per year on its own power. However, nematode infestation can spread substantial distances in a variety of ways. Anything that can move infested soil is capable of spreading the infestation, including farm machinery, vehicles and tools, wind, water, animals, and farm workers. Seed sized particles of soil often contaminate harvested seed. Consequently, nematode infestation can be spread when contaminated seed from infested fields is planted in non-infested fields. There is even evidence that certain nematode species can be spread by birds. Only some of these causes can be prevented.

Traditional practices for managing nematode infestation include: maintaining proper soil nutrients and soil pH levels in nematode-infested land; controlling other plant diseases, as well as insect and weed pests; using sanitation practices such as plowing, planting, and cultivating of nematode-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops; using nematicides; and planting resistant plant varieties.

Methods have been proposed for the genetic transformation of plants in order to confer increased resistance to plant parasitic nematodes. For example, a number of approaches involve transformation of plants with double-stranded RNA capable of inhibiting essential nematode genes. Other agricultural biotechnology approaches propose to over-express genes that encode proteins that are toxic to nematodes. U.S. Pat. Nos. 5,589,622 and 5,824,876 are directed to the identification of plant genes expressed specifically in or adjacent to the feeding site of the plant after attachment by the nematode.

US 2009/0089896 discloses a promoter of an Mtn21-like gene which is induced in syncytia of SCN-infected soybean. WO 2008/077892 discloses a promoter of a peroxidase-like gene which is induced in syncytia of SCN-infected soybean. WO 2008/071726 discloses a promoter of a trehalose-6-phosphate phosphatase-like gen which is induced in syncytia of SCN-infected soybean. WO 2008/095887 discloses a promoter of an Mtn3-like gene which is induced in syncytia of SCN-infected soybean. WO 2008/095888 discloses the promoter of an At5g12170-like gene which is induced in syncytia of SON-infected soybean.

A number of patent publications prophetically disclose and generically claim transgenic plants comprising any one or more of thousands of plant genes and having improved agronomic characteristics. Examples of such publications include US2004/0031072, US2006/0107345, US2004/0034888, US2004/0019927, US2004/0045049, US2004/0019927, US2006/0272060, WO2005/5112608, US2006/0150283, and US2007/0214517. Pathogen resistance, including nematode resistance, is disclosed as one potential improved agronomic characteristic of the transgenic plants described in these publications. However, none of these publications specifically associate any disclosed gene with improved nematode resistance in transgenic plants containing the gene.

Serine-Arginine rich (SR-rich) proteins are key regulators of plant gene expression, with various gene family members contributing to constitutive splicing of RNA, nuclear export, maintenance of mRNA stability and protein translation. SR proteins are also involved in alternative RNA splicing, where they bind specific RNA sequences and guide the formation of spliceosome complexes at weak splicing sites SR rich gene families are moderately populated in plants, with diverse sub-groups falling into approximately five motif-based categories.

The Avr9-elicited 111B-like gene is a transcription factor with sequence homology to 111B ACRE (Avr9/Cf-9 rapidly elicited) from Nicotiana tabacum and DREB1A/CBF3 from *Arabidopsis*. In tobacco the 111B ACRE gene is a pathogenesis-related transcriptional activator that is rapidly induced in lines expressing the Cf-9 resistance gene in response to Avr9 expressed by *Cladosporium fulvum*, a biotrophic fungus. In other species, CBF3/DREB1 genes are involved in activating abiotic stress response. U.S. Pat. No. 7,345,217 discloses SEQ ID NO:1408, an Avr9-elicited 111B-like gene which is purported to be a homolog of an *Arabidopsis thaliana* DNA designated G912. U.S. Pat. No. 7,345,217 generically discloses numerous categories of potential utilities for the thousands of genes disclosed therein, and one of those categories is identified as disease resistance, including nematode resistance. However, the only specific utilities proposed in U.S. Pat. No. 7,345,217 for G912 and its homologs are improved tolerances to cold, freezing, drought, and salt stress.

Basic Helix-Loop-Helix (bHLH) and Dehydration Responsive Element Binding (DREB) transcription factors are also key regulatory molecules in plants. The physiological functions of some bHLH genes have been demonstrated experimentally in plants. The R and TT8 genes are known to regulate anthocyanin accumulation in maize and *Arabidopsis*, and other bHLH genes interact with phytochrome and regulate light response. Other bHLH genes regulate hormone signaling. The physiological role of most plant bHLH genes is unknown, however, and there is little sequence conservation between bHLH gene family members outside of the core bHLH signature domain.

Dirigent-like proteins belong to a large, diverse gene family found in all major land plant groups analyzed to date. Dirigent-encoding genes cluster into 5 phylogenetic subfamilies, Dir-A through Dir-E. The Dir-A subfamily has been shown, in conjunction with phenolic oxidases, to direct the stereospecific assembly of lignins (cell wall components) and lignans (plant antioxidants and defense compounds) in a range of plant species. Expression of PsDIR1, a Dir-A gene from Pisum sativa, confers resistance to multiple fungal pathogens in transgenic canola. Dir-A subfamily genes are induced by a wide variety of stresses, such as mechanical wounding, herbivory and fungal infection. The specific biochemical functions of genes from subgroups Dir-B, Dir-C, Dir-D and Dir-E (Dir-like) proteins are not as well characterized, although genes from the Dir-C subfamily were shown to be induced by jasmonic acid treatment, salicylic acid and feeding by avirulent Hessian fly larvae.

To date, no genetically modified plant comprising a transgene capable of conferring nematode resistance has been deregulated in any country. Accordingly, a need continues to exist to identify safe and effective compositions and methods for controlling plant parasitic nematodes using agricultural biotechnology.

SUMMARY OF THE INVENTION

The present inventors have discovered that expression of a transgene comprising a polynucleotide encoding Serine-Arginine-rich protein, AVR9-elicited_111B-like protein, a bHLH protein, or a Dirigent-like protein in roots can render soybean plants resistant to SCN infection. Accordingly, the present invention provides transgenic plants and seeds, and methods to overcome, or at least alleviate, nematode infestation of valuable agricultural crops.

In one embodiment, the invention provides an isolated expression vector comprising a root-specific promoter in operative association with a polynucleotide selected from the group consisting of: a) a polynucleotide encoding a Serine-arginine rich protein; b) a polynucleotide encoding an AVR9-elicited_111B-like protein; c) a polynucleotide encoding a basic Helix-Loop-Helix protein; and d) a polynucleotide encoding a dirigent-like protein.

In another embodiment, the invention provides a method of making a nematode-resistant transgenic plant, the method comprising the steps of: a) providing a recombinant expression vector comprising a root-specific promoter in operative association with a polynucleotide selected from the group consisting of: i) a polynucleotide encoding a serine-arginine rich protein; ii) a polynucleotide encoding an AVR9-elicited_111B-like protein; iii) a polynucleotide encoding a basic Helix-Loop-Helix protein; and iv) a polynucleotide encoding a dirigent-like protein; b) transforming a plant cell with the recombinant expression vector; c) regenerating transgenic plants from the transformed plant cell; and d) selecting transgenic plants which demonstrate increased resistance to plant parasitic nematode infection when compared to wild type plants which do not comprise the recombinant expression vector.

In yet another embodiment, the invention provides a nematode-resistant transgenic plant comprising a recombinant expression vector comprising a root-specific promoter in operative association with a polynucleotide selected from the group consisting of: a) a polynucleotide encoding a serine-arginine rich protein; b) a polynucleotide encoding an AVR9-elicited_111B-like protein; c) a polynucleotide encoding a basic Helix-Loop-Helix protein; and d) a polynucleotide encoding a dirigent-like protein.

In another embodiment, the invention provides a seed which is true breeding for a transgene comprising a recombinant expression vector comprising a root-specific promoter in operative association with a polynucleotide selected from the group consisting of: a) a polynucleotide encoding a serine-arginine rich protein; b) a polynucleotide encoding an AVR9-elicited_111B-like protein; c) a polynucleotide encoding a basic Helix-Loop-Helix protein; and d) a polynucleotide encoding a dirigent-like protein.

BRIEF DESCRIPTION OF THE DRAWINGS

FIGS. 1*a*-1*b* show the table of SEQ ID NOs assigned to corresponding genes and promoters. SEQ ID NOs 1, 37, 39 and 49 correspond to full length *G. max* nucleotide sequences for polynucleotides encoding Serine/Arginine-rich protein (SEQ ID NO:1), Avr9-elicited 111b protein (SEQ ID NO:37), bHLH protein (SEQ ID NO:39) and Dirigent-like protein (SEQ ID NO:49), respectively. Syncytia-induced promoter sequences are given in SEQ ID NO:57 (TPP-like promoter from *A. thaliana*), SEQ ID NO:58 (MtN3-like promoter from *G. max*) and SEQ ID NO:59 (promoter from locus At5g12170 of *A. thaliana*). The constitutive ubiquitin promoter designated PcUbi4-2, from *P. crispum* is given in SEQ ID NO:60.

FIGS. 2a-2c show an amino acid alignment of exemplary Serine/Arginine-rich proteins performed using Vector NTI software suite v10.3.0 (gap opening penalty=10, gap extension penalty=0.05, gap separation penalty=8).

FIG. 3 shows an amino acid alignment of exemplary basic-helix-loop-helix proteins performed using Vector NTI software suite v10.3.0 (gap opening penalty=10, gap extension penalty=0.05, gap separation penalty=8).

FIG. 4 shows an amino acid alignment of exemplary Dirigent-like proteins performed using Vector NTI software suite v10.3.0 (gap opening penalty=10, gap extension penalty=0.05, gap separation penalty=8).

DETAILED DESCRIPTION OF THE PREFERRED EMBODIMENTS

The present invention may be understood more readily by reference to the following detailed description and the examples included herein. Throughout this application, various publications are referenced. The disclosures of all of these publications and those references cited within those publications in their entireties are hereby incorporated by reference into this application in order to more fully describe the state of the art to which this invention pertains. The terminology used herein is for the purpose of describing specific embodiments only and is not intended to be limiting. As used herein, "a" or "an" can mean one or more, depending upon the context in which it is used. Thus, for example, reference to "a cell" can mean that at least one cell can be used.

As used herein, the word "or" means any one member of a particular list and also includes any combination of members of that list.

As defined herein, a "transgenic plant" is a plant that has been altered using recombinant DNA technology to contain an isolated nucleic acid which would otherwise not be present in the plant. As used herein, the term "plant" includes a whole plant, plant cells, and plant parts. Plant parts include, but are not limited to, stems, roots, ovules, stamens, leaves, embryos, meristematic regions, callus tissue, gametophytes, sporophytes, pollen, microspores, and the like. The transgenic plant of the invention may be male sterile or male fertile, and may further include transgenes other than those that comprise the isolated polynucleotides described herein.

As defined herein, the term "nucleic acid" and "polynucleotide" are interchangeable and refer to RNA or DNA that is linear or branched, single or double stranded, or a hybrid thereof. The term also encompasses RNA/DNA hybrids. An "isolated" nucleic acid molecule is one that is substantially separated from other nucleic acid molecules which are present in the natural source of the nucleic acid (i.e., sequences encoding other polypeptides). For example, a cloned nucleic acid is considered isolated. A nucleic acid is also considered isolated if it has been altered by human intervention, or placed in a locus or location that is not its natural site, or if it is introduced into a cell by transformation. Moreover, an isolated nucleic acid molecule, such as a cDNA molecule, can be free from some of the other cellular material with which it is naturally associated, or culture medium when produced by recombinant techniques, or chemical precursors or other chemicals when chemically synthesized. While it may optionally encompass untranslated sequence located at both the 3' and 5' ends of the coding region of a gene, it may be preferable to remove the sequences which naturally flank the coding region in its naturally occurring replicon.

The term "gene" is used broadly to refer to any segment of nucleic acid associated with a biological function. Thus, genes include introns and exons as in genomic sequence, or just the coding sequences as in cDNAs and/or the regulatory sequences required for their expression. For example, gene refers to a nucleic acid fragment that expresses mRNA or functional RNA, or encodes a specific protein, and which includes regulatory sequences.

The terms "polypeptide" and "protein" are used interchangeably herein to refer to a polymer of consecutive amino acid residues.

The terms "operably linked" and "in operative association with" are interchangeable and as used herein refer to the association of isolated polynucleotides on a single nucleic acid fragment so that the function of one isolated polynucleotide is affected by the other isolated polynucleotide. For example, a regulatory DNA is said to be "operably linked to" a DNA that expresses an RNA or encodes a polypeptide if the two DNAs are situated such that the regulatory DNA affects the expression of the coding DNA.

The term "promoter" as used herein refers to a DNA sequence which, when ligated to a nucleotide sequence of interest, is capable of controlling the transcription of the nucleotide sequence of interest into mRNA. A promoter is typically, though not necessarily, located 5' (e.g., upstream) of a nucleotide of interest (e.g., proximal to the transcriptional start site of a structural gene) whose transcription into mRNA it controls, and provides a site for specific binding by RNA polymerase and other transcription factors for initiation of transcription.

The term "transcription regulatory element" as used herein refers to a polynucleotide that is capable of regulating the transcription of an operably linked polynucleotide. It includes, but not limited to, promoters, enhancers, introns, 5' UTRs, and 3' UTRs.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. In the present specification, "plasmid" and "vector" can be used interchangeably as the plasmid is the most commonly used form of vector. A vector can be a binary vector or a T-DNA that comprises the left border and the right border and may include a gene of interest in between. The term "expression vector" is interchangeable with the term "transgene" as used herein and means a vector capable of directing expression of a particular nucleotide in an appropriate host cell. The expression of the nucleotide can be over-expression. An expression vector comprises a regulatory nucleic acid element operably linked to a nucleic acid of interest, which is—optionally—operably linked to a termination signal and/or other regulatory element.

The term "homologs" as used herein refers to a gene related to a second gene by descent from a common ancestral DNA sequence. The term "homologs" may apply to the relationship between genes separated by the event of speciation (e.g., orthologs) or to the relationship between genes separated by the event of genetic duplication (e.g., paralogs).

As used herein, the term "orthologs" refers to genes from different species, but that have evolved from a common ancestral gene by speciation. Orthologs retain the same function in the course of evolution. Orthologs encode proteins having the same or similar functions. As used herein, the term "paralogs" refers to genes that are related by duplication within a genome. Paralogs usually have different functions or new functions, but these functions may be related.

The term "conserved region" or "conserved domain" as used herein refers to a region in heterologous polynucleotide or polypeptide sequences where there is a relatively high degree of sequence identity between the distinct sequences. The "conserved region" can be identified, for example, from the multiple sequence alignment using the Clustal W algorithm.

The term "cell" or "plant cell" as used herein refers to single cell, and also includes a population of cells. The population may be a pure population comprising one cell type. Likewise, the population may comprise more than one cell type. A plant cell within the meaning of the invention may be isolated (e.g., in suspension culture) or comprised in a plant tissue, plant organ or plant at any developmental stage.

The term "true breeding" as used herein refers to a variety of plant for a particular trait if it is genetically homozygous for that trait to the extent that, when the true-breeding variety is self-pollinated, a significant amount of independent segregation of the trait among the progeny is not observed.

The term "null segregant" as used herein refers to a progeny (or lines derived from the progeny) of a transgenic plant that does not contain the transgene due to Mendelian segregation.

The term "wild type" as used herein refers to a plant cell, seed, plant component, plant tissue, plant organ, or whole plant that has not been genetically modified or treated in an experimental sense.

The term "control plant" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated.

A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

The term "syncytia site" as used herein refers to the feeding site formed in plant roots after nematode infestation. The site is used as a source of nutrients for the nematodes. A syncytium is the feeding site for cyst nematodes and giant cells are the feeding sites of root knot nematodes.

In one embodiment, the invention provides an isolated expression vector comprising a root-specific promoter in operative association with a polynucleotide selected from the group consisting of: a) a polynucleotide encoding a serine-arginine rich protein; b) a polynucleotide encoding an AVR9-elicited_111B-like protein; c) a polynucleotide encoding a basic Helix-Loop-Helix protein; and d) a polynucleotide encoding a dirigent-like protein.

Any root-specific promoter may be employed in the expression vector of the invention. Exemplary root-specific promoters include, without limitation, the promoter derived from corn nicotianamine synthase gene (US 20030131377) and the rice RCC3 promoter (U.S. Ser. No. 11/075,113). Of particular utility in the present invention are root-specific promoters induced in nematode feeding sites (i.e., syncytia). Preferably, the Mtn3-like nematode-inducible promoter disclosed in WO 2008/095887, the nematode-inducible Mtn21-like promoter disclosed in US 2009/0089896, the nematode-inducible peroxidase-like promoter disclosed in WO 2008/077892, the nematode-inducible trehalose-6-phosphate phosphatase-like promoter disclosed in WO 2008/071726 and the nematode-inducible At5g12170-like promoter disclosed in WO 2008/095888 may be employed in the expression vector of the invention nematode-inducible.

Any polynucleotide encoding a serine-arginine rich protein may be employed in the isolated expression vector of the invention. Preferably, the polynucleotide encodes a serine-arginine rich protein selected from the group consisting of a polypeptide comprising amino acids 1 to 253 of SEQ ID NO: 2; a polypeptide comprising amino acids 1 to 249 of SEQ ID NO: 4; a polypeptide comprising amino acids 1 to 247 of SEQ ID NO: 6; a polypeptide comprising amino acids 1 to 249 of SEQ ID NO: 8; a polypeptide comprising amino acids 1 to 249 of SEQ ID NO: 10; a polypeptide comprising amino acids 1 to 245 of SEQ ID NO: 12; a polypeptide comprising amino acids 1 to 240 of SEQ ID NO: 14; a polypeptide comprising amino acids 1 to 261 of SEQ ID NO: 16; a polypeptide comprising amino acids 1 to 280 of SEQ ID NO: 18; a polypeptide comprising amino acids 1 to 248 of SEQ ID NO: 20; a polypeptide comprising amino acids 1 to 252 of SEQ ID NO: 22; a polypeptide comprising amino acids 1 to 265 of SEQ ID NO: 24; a polypeptide comprising amino acids 1 to 263 of SEQ ID NO: 26; a polypeptide comprising amino acids 1 to 220 of SEQ ID NO: 28; a polypeptide comprising amino acids 1 to 220 of SEQ ID NO: 30; a polypeptide comprising amino acids 1 to 263 of SEQ ID NO: 32; a polypeptide comprising amino acids 1 to 218 of SEQ ID NO: 34; and a polypeptide comprising amino acids 1 to 245 of SEQ ID NO: 36. More preferably, the polynucleotide encodes a serine-arginine rich protein comprising amino acids 1 to 253 of SEQ ID NO: 2.

Any polynucleotide encoding an AVR9-elicited_111B protein may be employed in the isolated expression vector of the invention. Preferably, the AVR9-elicited_111B protein comprises amino acids 1 to 226 of SEQ ID NO:38.

Any polynucleotide encoding a basic Helix-Loop-Helix protein may be employed in the isolated expression vector of invention. Preferably, the basic Helix-Loop-Helix protein is selected from the group consisting of a polypeptide comprising amino acids 1 to 231 of SEQ ID NO: 40; a polypeptide comprising amino acids 1 to 226 of SEQ ID NO: 42; a polypeptide comprising amino acids 1 to 232 of SEQ ID NO: 44; a polypeptide comprising amino acids 1 to 233 of SEQ ID NO: 46; and a polypeptide comprising amino acids 1 to 260 of SEQ ID NO: 48. More preferably, the basic Helix-Loop-Helix protein comprises amino acids 1 to 231 of SEQ ID NO: 40.

Any polynucleotide encoding a dirigent-like protein may be employed in the isolated expression vector of the invention. Preferably, the dirigent-like protein is selected from the group consisting of a polypeptide comprising amino acids 1 to 191 of SEQ ID NO: 50; a polypeptide comprising amino acids 1 to 191 of SEQ ID NO: 52; a polypeptide comprising amino acids 1 to 189 of SEQ ID NO: 54; and a polypeptide comprising amino acids 1 to 189 of SEQ ID NO: 56. More preferably, the dirigent-like protein comprises amino acids 1 to 191 of SEQ ID NO: 50.

In another embodiment, the isolated expression vector of the invention is employed in a method of making a nematode-resistant transgenic plant, the method comprising the steps of: a) providing the above-described recombinant expression vector b) transforming a plant cell with the recombinant expression vector; c) regenerating transgenic plants from the transformed plant cell; and d) selecting transgenic plants which demonstrate increased resistance to plant parasitic nematode infection when compared to wild type plants which do not comprise the recombinant expression vector.

A variety of methods for introducing polynucleotides into the genome of plants and for the regeneration of plants from plant tissues or plant cells are known in, for example, Plant Molecular Biology and Biotechnology (CRC Press, Boca Raton, Fla.), chapter 6/7, pp. 71-119 (1993); White F F (1993) Vectors for Gene Transfer in Higher Plants; Transgenic Plants, vol. 1, Engineering and Utilization, Ed.: Kung and Wu R, Academic Press, 15-38; Jenes B et al. (1993) Techniques for Gene Transfer; Transgenic Plants, vol. 1, Engineering and Utilization, Ed.: Kung and R. Wu, Academic Press, pp. 128-143; Potrykus (1991) Annu Rev Plant Physiol Plant Molec Biol 42:205-225; Halford N G, Shewry P R (2000) Br Med Bull 56(1):62-73.

Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13 mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of Agrobacterium (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). Agrobacterium based transformation techniques (especially for dicotyledonous plants) are well known in the art. The Agrobacterium strain (e.g., Agrobacterium tumefaciens or Agrobacterium rhizogenes) comprises a plasmid (Ti or Ri plasmid) and a T-DNA element which is transferred to the plant following infection with Agrobacterium. The T-DNA (transferred DNA) is integrated into the genome of the plant cell. The T-DNA may be localized on the Ri- or Ti-plasmid or is separately comprised in a so-called binary vector. Methods for the Agrobacterium-mediated transformation are described, for example, in Horsch RB et al. (1985) Science 225:1229. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225.

The nucleotides described herein can be directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit high expression levels. In one embodiment, the nucleotides are inserted into a plastid targeting vector and transformed into the plastid genome of a desired plant host. Plants homoplasmic for plastid genomes containing the nucleotide sequences are obtained, and are preferentially capable of high expression of the nucleotides. Plastid transformation technology is for example extensively described in U.S. Pat. Nos. 5,451,513, 5,545,817, 5,545,818, and 5,877,462 in WO 95/16783 and WO 97/32977, and in McBride et al. (1994) PNAS 91, 7301-7305.

The method described above produces another embodiment of the invention, a nematode-resistant transgenic plant comprising a recombinant expression vector comprising a root-specific promoter in operative association with a polynucleotide selected from the group consisting of: a) a polynucleotide encoding a serine-arginine rich protein; b) a polynucleotide encoding an AVR9-elicited_111B-like protein; c) a polynucleotide encoding a basic Helix-Loop-Helix protein; and d) a polynucleotide encoding a dirigent-like protein. The transgenic plants of the invention may be used to control infestation of a crop by a plant parasitic nematode.

The invention also provides a method of plant breeding, e.g., to prepare a crossed fertile transgenic plant. The transgenic plants of the invention may be crossed with similar transgenic plants or with transgenic plants lacking the nucleic acids of the invention or with non-transgenic plants, using known methods of plant breeding, to prepare seeds. Further, the transgenic plant of the present invention may comprise, and/or be crossed to another transgenic plant that comprises one or more nucleic acids, thus creating a "stack" of transgenes in the plant and/or its progeny. The seed is then planted to obtain a crossed fertile transgenic plant comprising the expression vector of the invention. The crossed fertile transgenic plant may have the expression vector inherited through a female parent or through a male parent. The second plant may be an inbred plant. The crossed fertile transgenic may be a hybrid.

"Gene stacking" can also be accomplished by transferring two or more genes into the cell nucleus by plant transformation. Multiple genes may be introduced into the cell nucleus during transformation either sequentially or in unison. In accordance with the invention, multiple genes encoding Serine-Arginine-rich, AVR9-elicited_111B-like, bHLH and Dirigent-like proteins can be stacked to provide enhanced nematode resistance. These stacked combinations can be created by any method including but not limited to cross-breeding plants by conventional methods or by genetic transformation. If the traits are stacked by genetic transformation, the Serine-Arginine-rich, AVR9-elicited_111B-like, bHLH and Dirigent-like proteins genes can be combined in any manner. For example if two genes are to be introduced, the two sequences can be contained in separate transformation cassettes or on the same transformation cassette. The expression of the sequences can be driven by the same or different promoters.

The transgenic plants described above produce yet another embodiment of the invention, a seed which is true breeding for a transgene comprising the recombinant expression vector comprising a root-specific promoter in operative association with a polynucleotide selected from the group consisting of: a) a polynucleotide encoding a serine-arginine rich protein; b) a polynucleotide encoding an AVR9-elicited_111B-like protein; c) a polynucleotide encoding a basic Helix-Loop-Helix protein; and d) a polynucleotide encoding a dirigent-like protein. The transgenic seeds of the invention may be used to control infestation of a crop by a plant parasitic nematode.

Crop plants and corresponding parasitic nematodes are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). For example, plant parasitic nematodes that are targeted by the present invention include, without limitation, cyst nematodes and root-knot nematodes. Specific plant parasitic nematodes which are targeted by the present invention include, without limitation, *Heterodera glycines, Heterodera schachtii, Heterodera avenae, Heterodera oryzae, Heterodera cajani, Heterodera trifolii, Globodera pallida, G. rostochiensis,* or *Globodera tabacum, Meloidogyne incognita, M. arenaria, M. hapla, M. javanica, M. naasi, M. exigua, Ditylenchus dipsaci, Ditylenchus angustus, Radopholus similis, Radopholus citrophilus, Helicotylenchus multicinctus, Pratylenchus coffeae, Pratylenchus brachyurus, Pratylenchus vulnus, Paratylenchus curvitatus, Paratylenchus zeae, Rotylenchulus reniformis, Paratrichodorus anemones, Paratrichodorus minor, Paratrichodorus christiei, Anguina tritici, Bidera avenae, Subanguina radicicola, Hoplolaimus seinhorsti, Hoplolaimus Columbus, Hoplolaimus galeatus, Tylenchulus semipenetrans, Hemicycliophora arenaria, Rhadinaphelenchus cocophilus, Belonolaimus longicaudatus, Trichodorus primitivus, Nacobbus aberrans, Aphelenchoides besseyi, Hemicriconemoides kanayaensis, Tylenchorhynchus claytoni, Xiphinema americanum, Cacopaurus pestis, Heterodera zeae, Heterodera filipjevi* and the like.

Plants which may be rendered nematode-resistant in accordance with the invention include monocotyledonous plants and dicotyledonous plants. Nematode-resistant plants produced in accordance with the invention include, without limitation, maize, wheat, rice, barley, oat, rye, sorghum, banana, and ryegrass. The plant can be from a genus selected from the group consisting of pea, alfalfa, soybean, carrot, celery, tomato, potato, cotton, tobacco, pepper, oilseed rape, beet, cabbage, cauliflower, broccoli, lettuce *A. thaliana*, and the like.

The invention is further illustrated by the following examples, which are not to be construed in any way as imposing limitations upon the scope thereof.

EXAMPLE 1

Vector Construction

Using a bioinformatics approach, four soybean genes, TA52573_3847 (SEQ ID NO:3), AVR9-elicited_111B (SEQ ID NO:37), GmbHLH_47172355 (SEQ ID NO:39), and GmDirigent_59580836 (SEQ ID NO:49) were identified as being down-regulated in syncytia of SCN-infected soybean roots, as compared to uninfected root tissue. As described herein, the gene designated TA52573_3847 SEQ ID NO:3 encodes a serine-arginine rich protein. The GmSerine-Arginine-rich gene (SEQ ID NO:1) employed in the isolated expression vectors described below encodes a protein having 93% sequence identity to TA52573_3847 (SEQ ID NO:3).

The constitutive ubiquitin promoter from parsley (WO 2003/102198; SEQ ID NO:60, designated PcUbi4) the nematode-inducible MtN3-like promoter from soybean (WO 2008/095887, SEQ ID NO:58), the nematode-inducible TPP-like promoter from *Arabidopsis* (WO 2008/071726, SEQ ID NO:57) and the constitutive Super Promoter (see U.S. Pat. No. 5,955,646) were used in to make the constructs described in Table 1 below.

TABLE 1

| Vector Name | Promoter | Gene Name | SEQ ID NO: of genes |
| --- | --- | --- | --- |
| RBM024 | PcUbi4 | GmSerine-Arginine-rich | SEQ ID NO: 1 |
| RBM036 | MtN3-like | GmSerine-Arginine-rich | SEQ ID NO: 1 |
| RBM019 | PcUbi4 | AVR9-elicited_111B | SEQ ID NO: 37 |
| RBM031 | MtN3-like | AVR9-elicited_111B | SEQ ID NO: 37 |
| RTP1124 | Super | AVR9-elicited_111B | SEQ ID NO: 37 |
| RTP1125 | TPP-like | AVR9-elicited_111B | SEQ ID NO: 37 |
| RTP1126 | PcUbi4 | GmbHLH_47172355 | SEQ ID NO: 39 |
| RTP1127 | MtN3-like | GmbHLH_47172355 | SEQ ID NO: 39 |
| RTP1086 | PcUbi4 | GmDirigent_59580836 | SEQ ID NO: 49 |
| RTP1090 | MtN3-like | GmDirigent_59580836 | SEQ ID NO: 49 |

The expression vectors also comprised the mutated form of the acetohydroxy acid synthase (AHAS) selection gene described in WO 2008/124495, which confers resistance to the herbicide ARSENAL (Imazapyr, BASF Corporation, Mount Olive, N.J.). The expression of AHAS2 was driven by the parsely ubiquitin promoter (SEQ ID NO:60).

EXAMPLE 2

Nematode Bioassay

A bioassay to assess nematode resistance conferred by the polynucleotides described herein was performed using a rooted plant assay system disclosed in commonly owned copending U.S. Ser. No. 12/001,234. Transgenic roots are generated after transformation with the binary vectors described in Example 1. Multiple transgenic root lines are sub-cultured and inoculated with surface-decontaminated race 3 SCN second stage juveniles (J2) at the level of about 500 J2/well. Four weeks after nematode inoculation, the cyst number in each well is counted. For each transformation construct, the number of cysts per line is calculated to determine the average cyst count and standard error for the construct. The cyst count values for each transformation construct is compared to the cyst count values of an empty vector control tested in parallel to determine if the construct tested results in a reduction in cyst count. Rooted explant cultures transformed with vectors RBM024, RBM036, RBM019, RBM031, RTP1124, RTP1125, RTP1126, RTP1127 and RTP1090 exhibited a general trend of reduced cyst numbers and female index relative to the known susceptible variety, Williams82. Transgenic roots expressing the GmDirigent_59580836 gene regulated by the constitutive PcUbi4 promoter (vector RTP1086) did not show reduced cyst counts relative to control lines. Some root lines constitutively expressing the GmSerine-Arginine-rich gene with the PcUbi4 promoter developed dark brown patches. The localization of dark brown patches varied among transgenic root lines, in some cases being limited to scattered individual cells, or lateral root emergence zones or extending entirely along the length of older roots. Transgenic roots over-expressing the AVR9-elicited_111B gene regulated by the constitutive PcUbi4 promoter (RBM019) or the constitutive Super promoter (RTP1124) developed thicker and shorter roots and reduced numbers of lateral roots relative to control lines.

The invention claimed is:

1. A method of making a nematode-resistant transgenic plant, the method comprising the steps of:

a) providing a recombinant expression vector comprising a root-specific promoter in operative association with a polynucleotide encoding an AVR9-elicited_111B-like protein comprising SEQ ID NO:38;

b) transforming a plant cell with the recombinant expression vector;

c) regenerating transgenic plants from the transformed plant cell; and d) selecting transgenic plants which demonstrate increased resistance to plant parasitic nematode infection when compared to wild type plants which do not comprise the recombinant expression vector.

2. A nematode-resistant transgenic plant comprising a recombinant expression vector comprising a root-specific promoter in operative association with a polynucleotide encoding an AVR9-elicited_111B-like protein comprising SEQ ID NO:38.

3. A seed which is true breeding for a transgene comprising a recombinant expression vector comprising a root-specific promoter in operative association with a polynucleotide encoding an AVR9-elicited_111B-like protein comprising SEQ ID NO:38.

4. An isolated expression vector comprising a root-specific promoter in operative association with a polynucleotide encoding an AVR9-elicited_111B-like protein comprising SEQ ID NO:38.

* * * * *

SEQUENCE LISTING

<160> NUMBER OF SEQ ID NOS: 60

<210> SEQ ID NO 1
<211> LENGTH: 762
<212> TYPE: DNA
<213> ORGANISM: Glycine max

<400> SEQUENCE: 1

```
atgagaggaa ggagctatag tccatcgcct cctcctccac gttacagcag aagaggagga      60
gggaggagtc ccagccctag gggccgctat cctccccgtc cccgacaaca agatctccct     120
accagccttc ttgttcgtaa ccttcgtcat gactgtaggc ctgaggatct tcgcagacct     180
tttggtcaat ttggtcctct caaggacatt taccttccta aggattacta cactggagaa     240
ccccgtggct ttggttttgt ccaatttgtg gatcctgcgg atgctgctga tgccaaatat     300
catatggatg gtcaagttct tcttggtcgg gagctcactg ttgttttttgc tgaagagaat     360
agaaagaagc caactgagat gaggacaaga gagagaaggg gtcgattttc tgatcgtagg     420
aggtctcctc ctcgttactc tcgttcacct cgctactctc gttcacctcg ctactctcgg     480
tctccaccac cacgtcatag atctcgttct cacagtcgtg actattattc tcctaaacga     540
agggagtatt caagatctgt ctcccctgag ggtagaaggt acagtcgaga agatcatat     600
tcacagcata atagagagag gtcattctca cgttccccac cttataatgg gggctcaagg     660
agccgtagtc agagtccagc aaagggccca ggccggagca ggagtccgag tctgaatcga     720
gatgaaaggg aaccagcccg aggtaggtcc cctagtcagt ga                         762
```

<210> SEQ ID NO 2
<211> LENGTH: 253
<212> TYPE: PRT
<213> ORGANISM: Glycine max

<400> SEQUENCE: 2

```
Met Arg Gly Arg Ser Tyr Ser Pro Ser Pro Pro Pro Arg Tyr Ser
1               5                   10                  15

Arg Arg Gly Gly Gly Arg Ser Pro Ser Pro Arg Gly Arg Tyr Pro Pro
            20                  25                  30

Arg Pro Arg Gln Gln Asp Leu Pro Thr Ser Leu Leu Val Arg Asn Leu
        35                  40                  45

Arg His Asp Cys Arg Pro Glu Asp Leu Arg Arg Pro Phe Gly Gln Phe
    50                  55                  60

Gly Pro Leu Lys Asp Ile Tyr Leu Pro Lys Asp Tyr Tyr Thr Gly Glu
65                  70                  75                  80

Pro Arg Gly Phe Gly Phe Val Gln Phe Val Asp Pro Ala Asp Ala Ala
                85                  90                  95

Asp Ala Lys Tyr His Met Asp Gly Gln Val Leu Leu Gly Arg Glu Leu
            100                 105                 110

Thr Val Val Phe Ala Glu Glu Asn Arg Lys Lys Pro Thr Glu Met Arg
        115                 120                 125

Thr Arg Glu Arg Arg Gly Arg Phe Ser Asp Arg Arg Ser Pro Pro
    130                 135                 140

Arg Tyr Ser Arg Ser Pro Arg Tyr Ser Arg Ser Pro Tyr Ser Arg
145                 150                 155                 160

Ser Pro Pro Pro Arg His Arg Ser Arg Ser His Ser Arg Asp Tyr Tyr
                165                 170                 175

Ser Pro Lys Arg Arg Glu Tyr Ser Arg Ser Val Ser Pro Glu Gly Arg
```

```
                    180                 185                 190
Arg Tyr Ser Arg Glu Arg Ser Tyr Ser Gln His Asn Arg Glu Arg Ser
                195                 200                 205

Phe Ser Arg Ser Pro Pro Tyr Asn Gly Gly Ser Arg Ser Arg Ser Gln
            210                 215                 220

Ser Pro Ala Lys Gly Pro Gly Arg Ser Arg Ser Pro Ser Leu Asn Arg
225                 230                 235                 240

Asp Glu Arg Glu Pro Ala Arg Gly Arg Ser Pro Ser Gln
                245                 250

<210> SEQ ID NO 3
<211> LENGTH: 750
<212> TYPE: DNA
<213> ORGANISM: Glycine max

<400> SEQUENCE: 3
atgagaggaa ggagctatag tccatcgcct cctccacgcc acagcagaag aggaggagga     60
gggaggagtc ccagcccag gggccgctat cctccccgtc cagacaaca agatctccct     120 accagccttc ttgtccgtaa ccttcgtcat gactgtaggc ctgaggatct acgccgacct    180
tttggtcaat ttggtcctct caaggacatt taccttccta aggattacta cactggagaa    240
ccccgtggct ttggttttgt ccaatatgtg gatcctgcgg atgctgctga tgctaaatat    300
catatggatg gtcaagttct tcttggtcgg gagctcactg ttgtctttgc tgaggagaat    360
agaaagaagc caactgagat gaggacacga gagagaaggg gtcgctttta tgatcgaagg    420
aggtctcctc ctcgttactc tcggtcaccc cgctactctc gatctccacc accacgccat    480
agatctcgtt ctcgcagtcg tgattattat tctcctcctg ccaaacgaag ggagtattca    540
agatctgtct cccctgagga tagaaggtac agtcgagaaa gatcattttc acagcatagt    600
agagagaggt catactcacg atctcctcct tataatgggg gctcaaggag tcgtagtcag    660
agtccagcaa agggcccagg tcagagcagg agtccaagtc cgaaccgaga tggaagggaa    720
ccagcccggg gtaggtcccc tagtcagtga                                     750

<210> SEQ ID NO 4
<211> LENGTH: 249
<212> TYPE: PRT
<213> ORGANISM: Glycine max

<400> SEQUENCE: 4

Met Arg Gly Arg Ser Tyr Ser Pro Ser Pro Pro Arg His Ser Arg
1               5                   10                  15

Arg Gly Gly Gly Gly Arg Ser Pro Ser Pro Arg Gly Arg Tyr Pro Pro
                20                  25                  30

Arg Pro Arg Gln Gln Asp Leu Pro Thr Ser Leu Leu Val Arg Asn Leu
            35                  40                  45

Arg His Asp Cys Arg Pro Glu Asp Leu Arg Arg Pro Phe Gly Gln Phe
        50                  55                  60

Gly Pro Leu Lys Asp Ile Tyr Leu Pro Lys Asp Tyr Tyr Thr Gly Glu
65                  70                  75                  80

Pro Arg Gly Phe Gly Phe Val Gln Tyr Val Asp Pro Ala Asp Ala Ala
                85                  90                  95

Asp Ala Lys Tyr His Met Asp Gly Gln Val Leu Leu Gly Arg Glu Leu
            100                 105                 110

Thr Val Val Phe Ala Glu Glu Asn Arg Lys Lys Pro Thr Glu Met Arg
        115                 120                 125
```

```
Thr Arg Glu Arg Arg Gly Arg Phe Tyr Asp Arg Arg Ser Pro Pro
        130                 135                 140
Arg Tyr Ser Arg Ser Pro Arg Tyr Ser Arg Ser Pro Pro Arg His
145                 150                 155                 160
Arg Ser Arg Ser Arg Ser Arg Asp Tyr Tyr Ser Pro Pro Ala Lys Arg
                165                 170                 175
Arg Glu Tyr Ser Arg Ser Val Ser Pro Glu Asp Arg Arg Tyr Ser Arg
            180                 185                 190
Glu Arg Ser Phe Ser Gln His Ser Arg Glu Arg Ser Tyr Ser Arg Ser
        195                 200                 205
Pro Pro Tyr Asn Gly Gly Ser Arg Ser Arg Ser Gln Ser Pro Ala Lys
    210                 215                 220
Gly Pro Gly Gln Ser Arg Ser Pro Ser Pro Asn Arg Asp Gly Arg Glu
225                 230                 235                 240
Pro Ala Arg Gly Arg Ser Pro Ser Gln
                245

<210> SEQ ID NO 5
<211> LENGTH: 744
<212> TYPE: DNA
<213> ORGANISM: Glycine max

<400> SEQUENCE: 5
atgagaggaa ggagctatag tccatcgcct cctcctccac gttacagcag aagaggagga      60
gggaggagtc ccagccctag ggccgctat cctccccgtc cccgacaaca agatctccct     120
accagccttc ttgttcgtaa ccttcgtcat gactgtaggc ctgaggatct tcgcatacct     180
tttggtcaat ttggtcctct caaggacatt taccttccta aggattacta cactggagaa     240
ccccgtggct ttggttttgt ccaatttgtg gatcctgcgg atgctgctga tgccaaatat     300
catatggatg gtcaagttct tcttggtcgg gagctcactg ttgttttttgc tgaagagaat     360 agaaagaagc caactgagat gaggacaaga gagagaaggg gtcgattttc tgatcgtagg     420
aggtctcctc ctcgttactc tcgttcacct cgctactctc ggtctccacc accacgtcat     480
agatctcgtt ctcacagtcg tgactattat tctcctaaac gaagggagta ttcaagatct     540
gtctcccctg agggtagaag gtacagtcga gaaagatcat attcacagca taatagagag     600
aggtcatact cacgttcccc accttataat ggggggctcaa ggagccgtag tcagagtcca     660
gcaaagggcc cagtccggag caggagtccg agtctgaatc gagatgaaag ggaaccagcc     720
cgaggtaggt cccccagtca gtga                                              744

<210> SEQ ID NO 6
<211> LENGTH: 247
<212> TYPE: PRT
<213> ORGANISM: Glycine max

<400> SEQUENCE: 6

Met Arg Gly Arg Ser Tyr Ser Pro Ser Pro Pro Pro Arg Tyr Ser
1               5                   10                  15
Arg Arg Gly Gly Gly Arg Ser Pro Ser Pro Arg Gly Arg Tyr Pro Pro
                20                  25                  30
Arg Pro Arg Gln Gln Asp Leu Pro Thr Ser Leu Leu Val Arg Asn Leu
            35                  40                  45
Arg His Asp Cys Arg Pro Glu Asp Leu Arg Ile Pro Phe Gly Gln Phe
        50                  55                  60
Gly Pro Leu Lys Asp Ile Tyr Leu Pro Lys Asp Tyr Tyr Thr Gly Glu
65                  70                  75                  80
```

Pro Arg Gly Phe Gly Phe Val Gln Phe Val Asp Pro Ala Asp Ala Ala
                85                  90                  95

Asp Ala Lys Tyr His Met Asp Gly Gln Val Leu Leu Gly Arg Glu Leu
            100                 105                 110

Thr Val Val Phe Ala Glu Glu Asn Arg Lys Lys Pro Thr Glu Met Arg
        115                 120                 125

Thr Arg Glu Arg Gly Arg Phe Ser Asp Arg Arg Ser Pro Pro
    130                 135                 140

Arg Tyr Ser Arg Ser Pro Arg Tyr Ser Arg Ser Pro Pro Arg His
145                 150                 155                 160

Arg Ser Arg Ser His Ser Arg Asp Tyr Tyr Ser Pro Lys Arg Glu
                165                 170                 175

Tyr Ser Arg Ser Val Ser Pro Glu Gly Arg Arg Tyr Ser Arg Glu Arg
            180                 185                 190

Ser Tyr Ser Gln His Asn Arg Glu Arg Ser Tyr Ser Arg Ser Pro Pro
        195                 200                 205

Tyr Asn Gly Gly Ser Arg Ser Arg Ser Gln Ser Pro Ala Lys Gly Pro
    210                 215                 220

Val Arg Ser Arg Ser Pro Ser Leu Asn Arg Asp Glu Arg Glu Pro Ala
225                 230                 235                 240

Arg Gly Arg Ser Pro Ser Gln
                245

<210> SEQ ID NO 7
<211> LENGTH: 750
<212> TYPE: DNA
<213> ORGANISM: unknown
<220> FEATURE:
<223> OTHER INFORMATION: Synthetic sequence

<400> SEQUENCE: 7

| | | | | | |
|---|---|---|---|---|---|
| atgagaggaa | ggagctatag | tccatcgcct | cctcctccac | gttacagcag | aagaggagga | 60 |
| gggaggagtc | ccagccctag | gggccgctat | cctccccgtc | ccagacaaca | agatctccct | 120 |
| accagccttc | ttgtccgtaa | ccttcgtcat | gactgtaggc | ctgaggatct | acgccgacct | 180 |
| tttggtcaat | ttggtcctct | caaggacatt | taccttccta | aggattacta | cactggagaa | 240 |
| ccccgtggct | ttgttttgt | ccaatatgtg | atcctgcgg | atgctgctga | tgctaaatat | 300 |
| catatggatg | gtcaagttct | tcttggtcgg | gagctcactg | ttgtctttgc | tgaggagaat | 360 |
| agaaagaagc | caactgagat | gaggacacga | gagagaaggg | gtcgctttta | tgatcgaagg | 420 |
| aggtctcctc | ctcgttactc | tcggtcaccc | cgctactctc | gatctccacc | accacgccat | 480 |
| agatctcgtt | ctcgcagtcg | tgattattat | tctcctcctg | ccaaacgaag | ggagtattca | 540 |
| agatctgtct | cccctgagga | tagaaggtac | agtcgagaaa | gatcattttc | acagcatagt | 600 |
| agagagaggt | catactcacg | atctcctcct | tataatgggg | gctcaaggag | tcgtagtcag | 660 |
| agtccagcaa | agggcccagg | tcagagcagg | agtccaagtc | cgaaccgaga | tggaagggaa | 720 |
| ccagcccggg | gtaggtcccc | tagtcagtga | | | | 750 |

<210> SEQ ID NO 8
<211> LENGTH: 249
<212> TYPE: PRT
<213> ORGANISM: Unknown
<220> FEATURE:
<223> OTHER INFORMATION: Synthetic sequence

<400> SEQUENCE: 8

```
Met Arg Gly Arg Ser Tyr Ser Pro Ser Pro Pro Pro Arg Tyr Ser
1               5                   10                  15
Arg Arg Gly Gly Gly Arg Ser Pro Ser Pro Arg Gly Arg Tyr Pro Pro
            20                  25                  30
Arg Pro Arg Gln Gln Asp Leu Pro Thr Ser Leu Leu Val Arg Asn Leu
        35                  40                  45
Arg His Asp Cys Arg Pro Glu Asp Leu Arg Arg Pro Phe Gly Gln Phe
    50                  55                  60
Gly Pro Leu Lys Asp Ile Tyr Leu Pro Lys Asp Tyr Tyr Thr Gly Glu
65                  70                  75                  80
Pro Arg Gly Phe Gly Phe Val Gln Tyr Val Pro Ala Asp Ala Ala
            85                  90                  95
Asp Ala Lys Tyr His Met Asp Gly Gln Val Leu Leu Gly Arg Glu Leu
        100                 105                 110
Thr Val Val Phe Ala Glu Glu Asn Arg Lys Lys Pro Thr Glu Met Arg
        115                 120                 125
Thr Arg Glu Arg Arg Gly Arg Phe Tyr Asp Arg Arg Ser Pro Pro
    130                 135                 140
Arg Tyr Ser Arg Ser Pro Arg Tyr Ser Arg Ser Pro Pro Arg His
145                 150                 155                 160
Arg Ser Arg Ser Arg Ser Arg Asp Tyr Tyr Ser Pro Ala Lys Arg
            165                 170                 175
Arg Glu Tyr Ser Arg Ser Val Ser Pro Glu Asp Arg Arg Tyr Ser Arg
            180                 185                 190
Glu Arg Ser Phe Ser Gln His Ser Arg Glu Arg Ser Tyr Ser Arg Ser
            195                 200                 205
Pro Pro Tyr Asn Gly Gly Ser Arg Ser Arg Ser Gln Ser Pro Ala Lys
210                 215                 220
Gly Pro Gly Gln Ser Arg Ser Pro Ser Pro Asn Arg Asp Gly Arg Glu
225                 230                 235                 240
Pro Ala Arg Gly Arg Ser Pro Ser Gln
                245
```

<210> SEQ ID NO 9
<211> LENGTH: 750
<212> TYPE: DNA
<213> ORGANISM: Populus tremula x Populus tremuloides

<400> SEQUENCE: 9

```
atgagaggaa ggagttatag tccatcacct ccaaggggct atagtagaag gggacggagt    60
cctagtcctc ggggacgtta tggtggacgt agtagggatc ttcctactag ccttctagtt   120
cgcaaccctc gtcatgattg caggccagaa gaccttcgca ggccatttga acagtttggt   180
gctcttaagg acatctactt gcctagagac tattatactg gggaaccccg tggttttggt   240
tttgtccaat atgcagatcc tcatgatgct gcagaggcaa acatcatat ggatggtcgt    300
gtctttcttg gccgggagtt gactgttgta tttgccgagg agaataggaa gaagccagtt   360
gatatgagag caagggagcg cacagccact aggggtcgag ttggcgatag aagaagatca   420
cctcctcgtt attctcggtc accacgccat tctcgttctc caccgccacg ccatgcaaca   480
tcccggtctc acagtcgtga ttttattcc cctccaaaaa gaaggcatca ctcaagatct   540
gtttcacccc gagagaggag gtacagtcaa gagaggtcat attcacgatc aaggagccac   600
agccaaactc caaataggg tcagatccgg agcccagcta ggagcccagc taggagccga    660
agccgtagcc caagaagaag cagaagccgt agcccaattc atgatgaata tcctaaagaa   720
```

```
gtaaatggag acaagtctcc tagtccataa                                      750
```

<210> SEQ ID NO 10
<211> LENGTH: 249
<212> TYPE: PRT
<213> ORGANISM: Populus tremula x Populus tremuloides

<400> SEQUENCE: 10

```
Met Arg Gly Arg Ser Tyr Ser Pro Ser Pro Pro Arg Gly Tyr Ser Arg
1               5                   10                  15

Arg Gly Arg Ser Pro Ser Pro Arg Gly Arg Tyr Gly Gly Arg Ser Arg
            20                  25                  30

Asp Leu Pro Thr Ser Leu Leu Val Arg Asn Leu Arg His Asp Cys Arg
        35                  40                  45

Pro Glu Asp Leu Arg Arg Pro Phe Glu Gln Phe Gly Ala Leu Lys Asp
    50                  55                  60

Ile Tyr Leu Pro Arg Asp Tyr Tyr Thr Gly Glu Pro Arg Gly Phe Gly
65                  70                  75                  80

Phe Val Gln Tyr Ala Asp Pro His Asp Ala Ala Glu Ala Lys His His
                85                  90                  95

Met Asp Gly Arg Val Phe Leu Gly Arg Glu Leu Thr Val Val Phe Ala
            100                 105                 110

Glu Glu Asn Arg Lys Lys Pro Val Asp Met Arg Ala Arg Glu Arg Thr
        115                 120                 125

Ala Thr Arg Gly Arg Val Gly Asp Arg Arg Ser Pro Pro Arg Tyr
    130                 135                 140

Ser Arg Ser Pro Arg His Ser Arg Ser Pro Pro Arg His Ala Thr
145                 150                 155                 160

Ser Arg Ser His Ser Arg Asp Phe Tyr Ser Pro Lys Arg Arg His
                165                 170                 175

His Ser Arg Ser Val Ser Pro Arg Glu Arg Tyr Ser Gln Glu Arg
            180                 185                 190

Ser Tyr Ser Arg Ser Arg Ser His Ser Gln Thr Pro Asn Arg Gly Gln
        195                 200                 205

Ile Arg Ser Pro Ala Arg Ser Pro Ala Arg Ser Arg Ser Arg Ser Pro
    210                 215                 220

Arg Arg Ser Arg Ser Arg Ser Pro Ile His Asp Glu Tyr Pro Lys Glu
225                 230                 235                 240

Val Asn Gly Asp Lys Ser Pro Ser Pro
                245
```

<210> SEQ ID NO 11
<211> LENGTH: 738
<212> TYPE: DNA
<213> ORGANISM: Populus trichocarpa

<400> SEQUENCE: 11

```
atgagaggaa ggagttatag tccatcacct ccaagggggct atagtagaag gggacggagt    60
cctagtcctc ggggacgtta tggtggacgt agtaggggatc ttcctactag ccttctagtt   120
cgcaacctcc gtcatgattg caggccagaa gaccttcgca ggccatttga acagtttggt   180
gctcttaagg acatctactt gcctagagac tattatactg gggaacccccg tggttttggt   240 tttgtccaat atgcagatcc tcatgatgct gcagaggcaa acatcatat ggatggtcga    300 gtctttcttg gccgggagtt gactgttgta tttgccgagg agaataggaa gaagccagtt    360
gatatgagag caagggagcg cacagccaca aggggtcgag ttggtgatag aagaagatca    420
```

| | | | | |
|---|---|---|---|---|
| cctcctcgtt | attctcggtc | accacgccat | tctcgttctc | caccgccacg ccatgcaaca | 480 |
| tcccggtctc | acagtcgtga | ttattattcc | cctccaaaaa | gaaggcatcc ctcaagatct | 540 |
| gtttcacccc | gagagaggag | gtacagtcaa | gagaggtcat | attcacgatc aaggagccac | 600 |
| agccaaactc | caaatagggg | tcagatccgg | agcccagtta | ggagccgaag cagtagccca | 660 |
| agaaaaagca | gaagccgtag | cccaattcat | gatgaatatc | ctaaagaagt aaatggagac | 720 |
| aagtctccta | gtccataa | | | | 738 |

<210> SEQ ID NO 12
<211> LENGTH: 245
<212> TYPE: PRT
<213> ORGANISM: Populus trichocarpa

<400> SEQUENCE: 12

Met Arg Gly Arg Ser Tyr Ser Pro Ser Pro Arg Gly Tyr Ser Arg
1               5                   10                  15
Arg Gly Arg Ser Pro Ser Pro Arg Gly Arg Tyr Gly Gly Arg Ser Arg
            20                  25                  30
Asp Leu Pro Thr Ser Leu Leu Val Arg Asn Leu Arg His Asp Cys Arg
        35                  40                  45
Pro Glu Asp Leu Arg Arg Pro Phe Glu Gln Phe Gly Ala Leu Lys Asp
    50                  55                  60
Ile Tyr Leu Pro Arg Asp Tyr Tyr Thr Gly Glu Pro Arg Gly Phe Gly
65                  70                  75                  80
Phe Val Gln Tyr Ala Asp Pro His Asp Ala Ala Glu Ala Lys His His
                85                  90                  95
Met Asp Gly Arg Val Phe Leu Gly Arg Glu Leu Thr Val Val Phe Ala
            100                 105                 110
Glu Glu Asn Arg Lys Lys Pro Val Asp Met Arg Ala Arg Glu Arg Thr
        115                 120                 125
Ala Thr Arg Gly Arg Val Gly Asp Arg Arg Ser Pro Pro Arg Tyr
    130                 135                 140
Ser Arg Ser Pro Arg His Ser Arg Ser Pro Pro Arg His Ala Thr
145                 150                 155                 160
Ser Arg Ser His Ser Arg Asp Tyr Tyr Ser Pro Pro Lys Arg His
                165                 170                 175
Pro Ser Arg Ser Val Ser Pro Arg Glu Arg Arg Tyr Ser Gln Glu Arg
            180                 185                 190
Ser Tyr Ser Arg Ser Arg Ser His Ser Gln Thr Pro Asn Arg Gly Gln
        195                 200                 205
Ile Arg Ser Pro Val Arg Ser Arg Ser Ser Pro Arg Lys Ser Arg
    210                 215                 220
Ser Arg Ser Pro Ile His Asp Glu Tyr Pro Lys Glu Val Asn Gly Asp
225                 230                 235                 240
Lys Ser Pro Ser Pro
            245

<210> SEQ ID NO 13
<211> LENGTH: 723
<212> TYPE: DNA
<213> ORGANISM: Brassica napus

<400> SEQUENCE: 13

| | | | | |
|---|---|---|---|---|
| atgaggggaa | ggagctacac | accatcacca | ccaaggggct | atgggaggag gggacggagc | 60 |
| cctagtcccc | gtggccgtta | cggtgggggt | cgtgacaggg | atctcccaac cagtcttttg | 120 |

| | |
|---|---|
| gttcgcaacc ttcgtcatga ttgcaggcaa gaggatctta ggaggccatt tgagcagttc | 180 |
| ggtcctgtca aggacatcta ccttccaagg gattattata ccggagatcc aagggggttt | 240 |
| ggtttcattc agtatgtgga ccctgctgat gctgcggagg caaaacatca catggaaggc | 300 |
| tatcttcttc ttggtcgtga gctgactgtt gtatttgcag aagagaacag gaagaagcca | 360 |
| actgaaatga ggacaaggga tcgaggtggt aggagcaaca gattcaatga cagaagacgt | 420 |
| tctcctcctc gctactctcg ttctccaccc cctcgacgtg gcggtagaac gcgatcacgt | 480 |
| agccgcgaat ataattctcc tcccctaaa agacatcagt ctaggtctgt ctcaccacag | 540 |
| gagagacgat acgagaagga gaggtcatac tctcgttcac caccacgcaa tggctcaagg | 600 |
| gctcgcagtg aagtcatga aaggcgaag aaaagctaca gcgggagcag agcccaaga | 660 |
| agaagcgtga gcccgagaag ggacagagct acactcctga acaagccagg agcctggtcc | 720 |
| tag | 723 |

<210> SEQ ID NO 14
<211> LENGTH: 240
<212> TYPE: PRT
<213> ORGANISM: Brassica napus

<400> SEQUENCE: 14

Met Arg Gly Arg Ser Tyr Thr Pro Ser Pro Arg Gly Tyr Gly Arg
1               5                   10                  15

Arg Gly Arg Ser Pro Ser Pro Arg Gly Arg Tyr Gly Gly Arg Asp
                20                  25                  30

Arg Asp Leu Pro Thr Ser Leu Leu Val Arg Asn Leu Arg His Asp Cys
                35                  40                  45

Arg Gln Glu Asp Leu Arg Arg Pro Phe Glu Gln Phe Gly Pro Val Lys
            50                  55                  60

Asp Ile Tyr Leu Pro Arg Asp Tyr Tyr Thr Gly Asp Pro Arg Gly Phe
65                  70                  75                  80

Gly Phe Ile Gln Tyr Val Asp Pro Ala Asp Ala Ala Glu Ala Lys His
                    85                  90                  95

His Met Glu Gly Tyr Leu Leu Leu Gly Arg Glu Leu Thr Val Val Phe
                100                 105                 110

Ala Glu Glu Asn Arg Lys Lys Pro Thr Glu Met Arg Thr Arg Asp Arg
                115                 120                 125

Gly Gly Arg Ser Asn Arg Phe Asn Asp Arg Arg Ser Pro Pro Arg
            130                 135                 140

Tyr Ser Arg Ser Pro Pro Arg Gly Gly Arg Thr Arg Ser Arg
145                 150                 155                 160

Ser Arg Glu Tyr Asn Ser Pro Pro Lys Arg His Gln Ser Arg Ser
                165                 170                 175

Val Ser Pro Gln Glu Arg Arg Tyr Glu Lys Glu Arg Ser Tyr Ser Arg
                180                 185                 190

Ser Pro Pro Arg Asn Gly Ser Arg Ala Arg Ser Gly Ser His Glu Lys
                195                 200                 205

Ala Lys Lys Ser Tyr Ser Gly Ser Arg Ser Pro Arg Arg Ser Val Ser
                210                 215                 220

Pro Arg Arg Asp Arg Ala Thr Leu Leu Asn Lys Pro Gly Ala Trp Ser
225                 230                 235                 240

<210> SEQ ID NO 15
<211> LENGTH: 786
<212> TYPE: DNA
<213> ORGANISM: Arabidopsis thaliana

<400> SEQUENCE: 15

```
atgagaggaa ggagctacac gccatcacca ccaagggggtt atggaaggag gggccggagc        60
cctagccctc ggggccggtt tggtgggagt cgtgacagtg atctcccaac cagtcttttg       120
gttcgcaact tacgtcatga ttgcaggcaa gaagacctca ggaggccatt tgagcagttt       180
ggtcccgtca aggacatcta ccttcctagg gattactata ctggagatcc aaggggggttt      240
ggattcattc agtttatgga tcctgctgat gctgctgagg ctaaacatca aatggatggt       300
tatcttcttc ttggtcgtga gttgactgtc gtatttgctg aagaaaaccg gaagaagcca       360
actgagatga gaacaaggga tcgaggtgga aggagcaaca gattccagga cagaagacgt       420
tctcctcctc ggtactctcg gtctcctcct cgccgtggtc gtagatcacg atcacgtagc       480
tgcggctata attctcctcc cgctaaaaga catcaatcta ggtctgtctc acctcaggat       540
agacgatatg agaaggagag gtcatactct cgctcaccac cccataatgg ctcaagggtt       600
cgcagtggaa gtcctgggag agtgaagagc acagcagaa gcccaagaag aagcgtgagc       660
ccaagaaaaa acaggagcta cacgccagaa caagcaagga gccaaagccc tgtccctagg       720
cagagcagga gcccgacccc agtccctcgt ggagcacaaa atggagaccg ttctccaagc       780
cagtga                                                                  786
```

<210> SEQ ID NO 16
<211> LENGTH: 261
<212> TYPE: PRT
<213> ORGANISM: Arabidopsis thaliana

<400> SEQUENCE: 16

```
Met Arg Gly Arg Ser Tyr Thr Pro Ser Pro Arg Gly Tyr Gly Arg
  1               5                  10                  15

Arg Gly Arg Ser Pro Ser Pro Arg Gly Arg Phe Gly Gly Ser Arg Asp
                 20                  25                  30

Ser Asp Leu Pro Thr Ser Leu Leu Val Arg Asn Leu Arg His Asp Cys
             35                  40                  45

Arg Gln Glu Asp Leu Arg Arg Pro Phe Glu Gln Phe Gly Pro Val Lys
         50                  55                  60

Asp Ile Tyr Leu Pro Arg Asp Tyr Tyr Thr Gly Asp Pro Arg Gly Phe
 65                  70                  75                  80

Gly Phe Ile Gln Phe Met Asp Pro Ala Asp Ala Ala Glu Ala Lys His
                 85                  90                  95

Gln Met Asp Gly Tyr Leu Leu Leu Gly Arg Glu Leu Thr Val Val Phe
                100                 105                 110

Ala Glu Glu Asn Arg Lys Lys Pro Thr Glu Met Arg Thr Arg Asp Arg
            115                 120                 125

Gly Gly Arg Ser Asn Arg Phe Gln Asp Arg Arg Ser Pro Pro Arg
        130                 135                 140

Tyr Ser Arg Ser Pro Pro Arg Arg Gly Arg Arg Ser Arg Ser Arg Ser
145                 150                 155                 160

Cys Gly Tyr Asn Ser Pro Pro Ala Lys Arg His Gln Ser Arg Ser Val
                165                 170                 175

Ser Pro Gln Asp Arg Arg Tyr Glu Lys Glu Arg Ser Tyr Ser Arg Ser
            180                 185                 190

Pro Pro His Asn Gly Ser Arg Val Arg Ser Gly Ser Pro Gly Arg Val
        195                 200                 205

Lys Ser His Ser Arg Ser Pro Arg Ser Val Ser Pro Arg Lys Asn
    210                 215                 220
```

Arg Ser Tyr Thr Pro Glu Gln Ala Arg Ser Gln Ser Pro Val Pro Arg
225                 230                 235                 240

Gln Ser Arg Ser Pro Thr Pro Val Pro Arg Gly Ala Gln Asn Gly Asp
            245                 250                 255

Arg Ser Pro Ser Gln
            260

<210> SEQ ID NO 17
<211> LENGTH: 843
<212> TYPE: DNA
<213> ORGANISM: Solanum tuberosum

<400> SEQUENCE: 17

```
atgagggaa gaagttacag cccctcaccc cctagaggct atggaaggag aggaaggagc    60
ccaagcccca gaggggtcg ctatggtggt cgtagcagag atgatccaac tactctatta   120
gtgcgcaatc ttcgccatga ctgtcggcca gaggacctca aaaaaccatt cgggcaaatt   180
ggtcctgtca aggacattta cttgccaagg actattata ctcgtgaacc acgtggtttt   240
ggatttatcc aatatctgga tcctgctgat gcagcagaag ctaagtatca gatggatggt   300
caggctttcc aaggtcggca actgacagta gttttgctg aggagaacag gaaaaagcct   360
caagaaatga gctaggga gcgtggaagt ggtaggggtg ccgcaacta tgatcggaga   420
ggtactcccc ctaggtacca taactctcct cggtattcac gatctccacc tccccgcggc   480
cgtgattact actctccacc taagagaagg caatactcaa ggtctgtttc gcctgaagag   540
aaaagataca gtcgtgagag atcatattct cctcgtggtg gtcagggaag gcatactca   600
caatcccctc ctagggagca gtctccacca ttcaatgggt caagaagccg cagtcaaagt   660
ccagtcaggg agcattctcc accttataat ggttcaagga gtcgcagccg gagtccagtt   720
agggcacgtt ctccagttag gggtcacagc aggaggctga ccctagtca aggccatagt   780
aggagccctg atgctgtcca ttattccagg aatcctgacc atgacgtgtc cccgagacac   840
tga                                                                843
```

<210> SEQ ID NO 18
<211> LENGTH: 280
<212> TYPE: PRT
<213> ORGANISM: Solanum tuberosum

<400> SEQUENCE: 18

Met Arg Gly Arg Ser Tyr Ser Pro Ser Pro Arg Gly Tyr Gly Arg
1                   5                   10                  15

Arg Gly Arg Ser Pro Ser Pro Arg Gly Gly Arg Tyr Gly Gly Arg Ser
                20                  25                  30

Arg Asp Asp Pro Thr Thr Leu Leu Val Arg Asn Leu Arg His Asp Cys
            35                  40                  45

Arg Pro Glu Asp Leu Lys Lys Pro Phe Gly Gln Ile Gly Pro Val Lys
        50                  55                  60

Asp Ile Tyr Leu Pro Arg Asp Tyr Tyr Thr Arg Glu Pro Arg Gly Phe
65                  70                  75                  80

Gly Phe Ile Gln Tyr Leu Asp Pro Ala Asp Ala Ala Glu Ala Lys Tyr
                85                  90                  95

Gln Met Asp Gly Gln Ala Phe Gln Gly Arg Gln Leu Thr Val Val Phe
            100                 105                 110

Ala Glu Glu Asn Arg Lys Lys Pro Gln Glu Met Arg Ala Arg Glu Arg
        115                 120                 125

```
Gly Ser Gly Arg Gly Gly Arg Asn Tyr Asp Arg Arg Gly Thr Pro Pro
            130                 135                 140

Arg Tyr His Asn Ser Pro Arg Tyr Ser Arg Ser Pro Pro Pro Arg Gly
145                 150                 155                 160

Arg Asp Tyr Tyr Ser Pro Pro Lys Arg Arg Gln Tyr Ser Arg Ser Val
                165                 170                 175

Ser Pro Glu Glu Lys Arg Tyr Ser Arg Glu Arg Ser Tyr Ser Pro Arg
            180                 185                 190

Gly Gly Gln Gly Arg Ala Tyr Ser Gln Ser Pro Pro Arg Glu Gln Ser
        195                 200                 205

Pro Pro Phe Asn Gly Ser Arg Ser Arg Ser Gln Ser Pro Val Arg Glu
    210                 215                 220

His Ser Pro Pro Tyr Asn Gly Ser Arg Ser Arg Ser Arg Ser Pro Val
225                 230                 235                 240

Arg Ala Arg Ser Pro Val Arg Gly His Ser Arg Arg Leu Ser Pro Ser
                245                 250                 255

Gln Gly His Ser Arg Ser Pro Asp Ala Val His Tyr Ser Arg Asn Pro
            260                 265                 270

Asp His Asp Val Ser Pro Arg His
            275                 280

<210> SEQ ID NO 19
<211> LENGTH: 747
<212> TYPE: DNA
<213> ORGANISM: Solanum tuberosum

<400> SEQUENCE: 19
atgaggagga gaagttacag cccatcacca cagagaggtt atggcagaag aggaaggagt    60
ccgagtccca gaggtcgata tggtggtcat agtagagatg gtccgactag tcttttagtt   120
cgaaatcttc gccatgattg tcggccagaa gacctcagaa ggccgttcgg gcaatttggc   180
cctgtgaagg atatttactt gccaaaggac tactacactg gtgaaccacg aggctttgga   240
tttgtccagt ttgtggatcc tgctgatgct gcagatgcca agtatcagat ggatggacaa   300
ggttttcaag gtcggcaact gactgtggtt tttgccgagg aaaacaggaa aaaacctact   360
gaaatgagat ctagggaacg cagtggaagt cataggagta gccgcagcca tgatcggaga   420
cgtactccac cttcacggta tgcaagagca ggatcacaca gccgtgatta ctctcccaag   480
agaaggcagt actcgaggtc tgtctcacct gaagagaaaa gatacagtcg tgagaggtca   540
tattcacgat ccctcctcg tggccttct cctccaccac ataatgggtc aaggagtcgc   600
agtcaaactc cagtcagaga gcgcccacca tataatggca gtccaaggag ccgtagcaga   660
agtccagtta ggagggagcg ttctccggtt agggtcaca gcaggagccc tagtaggagc   720
cctggttgtg ctccctactc gccatga                                       747

<210> SEQ ID NO 20
<211> LENGTH: 248
<212> TYPE: PRT
<213> ORGANISM: Solanum tuberosum

<400> SEQUENCE: 20

Met Arg Arg Arg Ser Tyr Ser Pro Ser Pro Gln Arg Gly Tyr Gly Arg
1               5                   10                  15

Arg Gly Arg Ser Pro Ser Pro Arg Gly Arg Tyr Gly Gly His Ser Arg
            20                  25                  30

Asp Gly Pro Thr Ser Leu Leu Val Arg Asn Leu Arg His Asp Cys Arg
        35                  40                  45
```

Pro Glu Asp Leu Arg Arg Pro Phe Gly Gln Phe Gly Pro Val Lys Asp
        50                  55                  60

Ile Tyr Leu Pro Lys Asp Tyr Tyr Thr Gly Glu Pro Arg Gly Phe Gly
 65                  70                  75                  80

Phe Val Gln Phe Val Asp Pro Ala Asp Ala Ala Asp Ala Lys Tyr Gln
                 85                  90                  95

Met Asp Gly Gln Gly Phe Gln Gly Arg Gln Leu Thr Val Val Phe Ala
            100                 105                 110

Glu Glu Asn Arg Lys Lys Pro Thr Glu Met Arg Ser Arg Glu Arg Ser
            115                 120                 125

Gly Ser His Arg Ser Ser Arg Ser His Asp Arg Arg Thr Pro Pro
        130                 135                 140

Ser Arg Tyr Ala Arg Ala Gly Ser His Ser Arg Asp Tyr Ser Pro Lys
145                 150                 155                 160

Arg Arg Gln Tyr Ser Arg Ser Val Ser Pro Glu Glu Lys Arg Tyr Ser
                165                 170                 175

Arg Glu Arg Ser Tyr Ser Arg Ser Pro Pro Arg Gly Leu Ser Pro Pro
            180                 185                 190

Pro His Asn Gly Ser Arg Ser Ser Gln Thr Pro Val Arg Glu Arg
        195                 200                 205

Pro Pro Tyr Asn Gly Ser Pro Arg Ser Arg Ser Arg Ser Pro Val Arg
    210                 215                 220

Arg Glu Arg Ser Pro Val Arg Gly His Ser Arg Ser Pro Ser Arg Ser
225                 230                 235                 240

Pro Gly Cys Ala Pro Tyr Ser Pro
                245

<210> SEQ ID NO 21
<211> LENGTH: 759
<212> TYPE: DNA
<213> ORGANISM: Solanum lycopersicon

<400> SEQUENCE: 21
atgaggagga gaagttacag cccatcacca ccaagaggtt atggcagaag aggaaggagt    60
ccaagtccca gaggtcgata tgctggtcat ggtagagatg gtccgactag tcttttagtt   120
cgaaaccttc gccatgattg tcggccagaa gacctcagga ggccattcgg caatttggc    180 cctgtgaagg atatttactt gccaaaggac tactacactg gtgaaccacg aggctttgga   240
tttgtccagt ttgtggatcc tgctgatgct gcagatgcta gtatcagat ggatggacaa    300 ggttttcaag gtcggcaact gactgtggtt tttgcagagg aaaacaggaa aaaacctact   360
gaaatgagat ctagggaacg cagtggaagt cataggagta gccgcagcta tgataggaga   420
cgtactccac cttcacgtta tgcaagacca ggatcacaca gccgtgatta ctctcccaag   480
agaaggccgt actcgaggtc tgtctcacct gaagagaaaa gatacagtcg tgagaggtca   540
tattcacgat ccctcctcg ggacctgtct cctccaccac ataatggatc aaggagtcga   600
agtcaaactc cagtcagaga gcacccacca tacaatggca gtccaaggag ccgtagcaga   660
agtccagtta ggagggagcg ttctccagtt aggggtcaca gcaggagccc tagtaggagc   720
cgtagcagga gccctggttg tgctccctac tcaccatga                           759

<210> SEQ ID NO 22
<211> LENGTH: 252
<212> TYPE: PRT
<213> ORGANISM: Solanum lycopersicon -continued

<400> SEQUENCE: 22

```
Met Arg Arg Arg Ser Tyr Ser Pro Ser Pro Arg Gly Tyr Gly Arg
1               5                   10                  15

Arg Gly Arg Ser Pro Ser Pro Arg Gly Arg Tyr Ala Gly His Gly Arg
            20                  25                  30

Asp Gly Pro Thr Ser Leu Leu Val Arg Asn Leu Arg His Asp Cys Arg
            35                  40                  45

Pro Glu Asp Leu Arg Arg Pro Phe Gly Gln Phe Gly Pro Val Lys Asp
        50                  55                  60

Ile Tyr Leu Pro Lys Asp Tyr Tyr Thr Gly Glu Pro Arg Gly Phe Gly
65                  70                  75                  80

Phe Val Gln Phe Val Asp Pro Ala Asp Ala Ala Asp Ala Lys Tyr Gln
                85                  90                  95

Met Asp Gly Gln Gly Phe Gln Gly Arg Gln Leu Thr Val Val Phe Ala
            100                 105                 110

Glu Glu Asn Arg Lys Lys Pro Thr Glu Met Arg Ser Arg Glu Arg Ser
        115                 120                 125

Gly Ser His Arg Ser Ser Arg Ser Tyr Asp Arg Arg Thr Pro Pro
    130                 135                 140

Ser Arg Tyr Ala Arg Pro Gly Ser His Ser Arg Asp Tyr Ser Pro Lys
145                 150                 155                 160

Arg Arg Pro Tyr Ser Arg Ser Val Ser Pro Glu Glu Lys Arg Tyr Ser
                165                 170                 175

Arg Glu Arg Ser Tyr Ser Arg Ser Pro Pro Arg Asp Leu Ser Pro Pro
            180                 185                 190

Pro His Asn Gly Ser Arg Ser Arg Ser Gln Thr Pro Val Arg Glu His
        195                 200                 205

Pro Pro Tyr Asn Gly Ser Pro Arg Ser Arg Ser Arg Ser Pro Val Arg
    210                 215                 220

Arg Glu Arg Ser Pro Val Arg Gly His Ser Arg Ser Pro Ser Arg Ser
225                 230                 235                 240

Arg Ser Arg Ser Pro Gly Cys Ala Pro Tyr Ser Pro
                245                 250
```

<210> SEQ ID NO 23
<211> LENGTH: 798
<212> TYPE: DNA
<213> ORGANISM: Nicotiana benthamiana

<400> SEQUENCE: 23

```
atgaggagac ggagttacag cccatcacca ccgcgaggtt atggcagcag aggcgggagg    60
agcccgagcc ccaggggtcg atatggtggt cgtagcagag atgctcctac tagtctctta   120
gttcgaaatc ttcgccatga ttgtcggcca gaagacctaa gaaggccgtt cgggcaattt   180
gggcctgtca aggacattta cttgcccagg gactactaca ctggtcaacc acgtggcttt   240
ggatttgtcc agtttgtgga tcctgctgat gctgctgaag ccaagtatca gatggatggg   300
cagggttttc agggtcggca actgactgtg gtttttgctg aggaaaacag gaaaagcca   360
actgaaatga gagctaggga acgtagtgga agtggtagga gccgcagcta tgatcggaga   420
cggtactcac ctcaatattc cagatctcca cctccacgtt atgcaaggtc accatcccgc   480
agccatggct actctcctaa gagaaggcag tactcgaggt ctgtttcacc tgaagagaaa   540
agatacagcc gtgagagatc atactcgcgt tcccctgcaa gggacatttc tccaccctat   600
aatgggtcaa ggagccgcag tcaaactcca gtcagaaagc attctccata tgatgatggt   660
```

```
cgaaggagcc gcagcagaag tccagttaag gagcgttttg cggttagggt tcacagcagg      720
agccccagtc gcagcaggag cccaggtgat gtccattact cgagggatcc agatcatgac      780
gtgtctccac gacactga                                                   798
```

<210> SEQ ID NO 24
<211> LENGTH: 265
<212> TYPE: PRT
<213> ORGANISM: Nicotiana benthamiana

<400> SEQUENCE: 24

```
Met Arg Arg Arg Ser Tyr Ser Pro Ser Pro Arg Gly Tyr Gly Ser
1               5                   10                  15

Arg Gly Gly Arg Ser Pro Ser Pro Arg Gly Arg Tyr Gly Gly Arg Ser
            20                  25                  30

Arg Asp Ala Pro Thr Ser Leu Leu Val Arg Asn Leu Arg His Asp Cys
        35                  40                  45

Arg Pro Glu Asp Leu Arg Arg Pro Phe Gly Gln Phe Gly Pro Val Lys
    50                  55                  60

Asp Ile Tyr Leu Pro Arg Asp Tyr Tyr Thr Gly Gln Pro Arg Gly Phe
65                  70                  75                  80

Gly Phe Val Gln Phe Val Asp Pro Ala Asp Ala Glu Ala Lys Tyr
                85                  90                  95

Gln Met Asp Gly Gln Gly Phe Gln Gly Arg Gln Leu Thr Val Val Phe
            100                 105                 110

Ala Glu Glu Asn Arg Lys Lys Pro Thr Glu Met Arg Ala Arg Glu Arg
        115                 120                 125

Ser Gly Ser Gly Arg Ser Arg Ser Tyr Asp Arg Arg Tyr Ser Pro
    130                 135                 140

Gln Tyr Ser Arg Ser Pro Pro Arg Tyr Ala Arg Ser Pro Ser Arg
145                 150                 155                 160

Ser His Gly Tyr Ser Pro Lys Arg Arg Gln Tyr Ser Arg Ser Val Ser
                165                 170                 175

Pro Glu Glu Lys Arg Tyr Ser Arg Glu Arg Ser Tyr Ser Arg Ser Pro
            180                 185                 190

Ala Arg Asp Ile Ser Pro Pro Tyr Asn Gly Ser Arg Ser Arg Ser Gln
        195                 200                 205

Thr Pro Val Arg Lys His Ser Pro Tyr Asp Asp Gly Arg Arg Ser Arg
    210                 215                 220

Ser Arg Ser Pro Val Lys Glu Arg Phe Ala Val Arg Val His Ser Arg
225                 230                 235                 240

Ser Pro Ser Arg Ser Arg Ser Pro Gly Asp Val His Tyr Ser Arg Asp
                245                 250                 255

Pro Asp His Asp Val Ser Pro Arg His
            260                 265
```

<210> SEQ ID NO 25
<211> LENGTH: 792
<212> TYPE: DNA
<213> ORGANISM: Nicotiana tabacum

<400> SEQUENCE: 25

```
atgaggagac ggagttacag cccatcacca ccacgaggtt atggcaggag aggagggagg       60
agcccgagcc ccaggggtcg atatggtggt cgtagcagag atgctcctac tagtctctta      120
gttcgaaatc ttcgccatga ttgtcggcca agagacctaa gaggccgtt cgggcaattt       180 gggcctgtca aggacattta cttgcccagg gactactaca ctggtcaacc acgtggcttt      240
```

```
ggatttgtcc agtttgtgga tccagctgat gctgcagaag ctaagtatca gatggatggg      300
cagggttttc aaggtcggca actgactgtg gtttttgcag aggaaaacag gaaaaagcca      360
actgaaatga gagctaggga acgtagtgga agtggtagga gccgcagcta tgatcggaga      420
cggtactcac ctcaatattc cagatctcca cctccacgtt atgcaaggtc ccgcagccgt      480
ggctactctc ctaagagaag gcagtactcg aggtctgttt cacctgaaga gaaaagatac      540
agccgtgaga gatcatactc acgttcccct gcaagggaca tttctccacc atataatggg      600
tcaaggagtc gcagtcaaac tccggtcaga gagcattcac catatgatga tggtcgaagg      660
agccgcagca gaagtccagt taaggagcgt tctccggtta ggggtcacag caggagtccc      720
agtcgcagca ggagcccagg tgatgtccgt tactcgaggg atccagatca tgacgtgtct      780
ccacgacact ga                                                         792

<210> SEQ ID NO 26
<211> LENGTH: 263
<212> TYPE: PRT
<213> ORGANISM: Nicotiana tabacum

<400> SEQUENCE: 26

Met Arg Arg Arg Ser Tyr Ser Pro Ser Pro Arg Gly Tyr Gly Arg
1               5                   10                  15

Arg Gly Gly Arg Ser Pro Ser Pro Arg Gly Arg Tyr Gly Gly Arg Ser
            20                  25                  30

Arg Asp Ala Pro Thr Ser Leu Leu Val Arg Asn Leu Arg His Asp Cys
        35                  40                  45

Arg Pro Glu Asp Leu Arg Arg Pro Phe Gly Gln Phe Gly Pro Val Lys
    50                  55                  60

Asp Ile Tyr Leu Pro Arg Asp Tyr Tyr Thr Gly Gln Pro Arg Gly Phe
65                  70                  75                  80

Gly Phe Val Gln Phe Val Asp Pro Ala Asp Ala Glu Ala Lys Tyr
                85                  90                  95

Gln Met Asp Gly Gln Gly Phe Gln Gly Arg Gln Leu Thr Val Val Phe
            100                 105                 110

Ala Glu Glu Asn Arg Lys Lys Pro Thr Glu Met Arg Ala Arg Glu Arg
        115                 120                 125

Ser Gly Ser Gly Arg Ser Arg Ser Tyr Asp Arg Arg Tyr Ser Pro
    130                 135                 140

Gln Tyr Ser Arg Ser Pro Pro Arg Tyr Ala Arg Ser Arg Ser Arg
145                 150                 155                 160

Gly Tyr Ser Pro Lys Arg Arg Gln Tyr Ser Arg Ser Val Ser Pro Glu
                165                 170                 175

Glu Lys Arg Tyr Ser Arg Glu Arg Ser Tyr Ser Arg Ser Pro Ala Arg
            180                 185                 190

Asp Ile Ser Pro Pro Tyr Asn Gly Ser Arg Ser Arg Ser Gln Thr Pro
        195                 200                 205

Val Arg Glu His Ser Pro Tyr Asp Asp Gly Arg Ser Arg Ser Arg
    210                 215                 220

Ser Pro Val Lys Glu Arg Ser Pro Val Arg Gly His Ser Arg Ser Pro
225                 230                 235                 240

Ser Arg Ser Arg Ser Pro Gly Asp Val Arg Tyr Ser Arg Asp Pro Asp
                245                 250                 255

His Asp Val Ser Pro Arg His
            260
```

<210> SEQ ID NO 27
<211> LENGTH: 663
<212> TYPE: DNA
<213> ORGANISM: Medicago truncatula

<400> SEQUENCE: 27

| | | |
|---|---|---|
| atgaggggaa gaagttacag ttacagtcct tcacctccaa ggcgttatgg tggaaggaga | 60 |
| cgcagtccga gtccaagagg ccggtatgga ggacgttata gaggtggccg tgatagggat | 120 |
| ctgcctacaa gtcttctcgt ccgaaacctg gccaagatt gcaggccaga agatctgcac | 180 |
| gatccatttg gacagtttgg tcctgtcaag gatgtttacc tgcctcgtga ttattatact | 240 |
| ggggagccaa ggggttttgg gtttgttcaa tttgtggatc cagctgatgc tgccgatgcg | 300 |
| aaatatcaca tggatggtca agttcttctt ggccgtgagt taactgtggt gtttgctgaa | 360 |
| gaaaacagaa agaaacctca agaaatgaga gcaagagaac gtgggaggtc atatgattat | 420 |
| aggcgatctc cacgtcgtcg ttctcgttca ccacgctatg ctcgaaccta ttctcgtagt | 480 |
| ccagactata caccttcacc aagaccaagg cgatattcca ggtccatctc accaagagac | 540 |
| gaaaggtata ggagacggtc atactctaga tccccttaca gatcacctta tggatctaga | 600 |
| agccctgatc gaggtaggag ttacagcagg agcataagcc gcagtccagg gtactcaagg | 660 |
| tga | 663 |

<210> SEQ ID NO 28
<211> LENGTH: 220
<212> TYPE: PRT
<213> ORGANISM: Medicago truncatula

<400> SEQUENCE: 28

Met Arg Gly Arg Ser Tyr Ser Tyr Ser Pro Ser Pro Arg Arg Tyr
1               5                   10                  15

Gly Gly Arg Arg Arg Ser Pro Ser Pro Arg Gly Arg Tyr Gly Gly Arg
            20                  25                  30

Tyr Arg Gly Gly Arg Asp Arg Asp Leu Pro Thr Ser Leu Leu Val Arg
        35                  40                  45

Asn Leu Ala Lys Asp Cys Arg Pro Glu Asp Leu His Asp Pro Phe Gly
    50                  55                  60

Gln Phe Gly Pro Val Lys Asp Val Tyr Leu Pro Arg Asp Tyr Tyr Thr
65                  70                  75                  80

Gly Glu Pro Arg Gly Phe Gly Phe Val Gln Phe Val Asp Pro Ala Asp
                85                  90                  95

Ala Ala Asp Ala Lys Tyr His Met Asp Gly Gln Val Leu Leu Gly Arg
            100                 105                 110

Glu Leu Thr Val Val Phe Ala Glu Glu Asn Arg Lys Lys Pro Gln Glu
        115                 120                 125

Met Arg Ala Arg Glu Arg Gly Arg Ser Tyr Asp Tyr Arg Arg Ser Pro
    130                 135                 140

Arg Arg Arg Ser Arg Ser Pro Arg Tyr Ala Arg Thr Tyr Ser Arg Ser
145                 150                 155                 160

Pro Asp Tyr Thr Pro Ser Pro Arg Pro Arg Arg Tyr Ser Arg Ser Ile
                165                 170                 175

Ser Pro Arg Asp Glu Arg Tyr Arg Arg Ser Tyr Ser Arg Ser Pro
            180                 185                 190

Tyr Arg Ser Pro Tyr Gly Ser Arg Ser Pro Asp Arg Gly Arg Ser Tyr
        195                 200                 205

Ser Arg Ser Ile Ser Arg Ser Pro Gly Tyr Ser Arg
    210                 215                 220

```
                   210                 215                 220
```

<210> SEQ ID NO 29
<211> LENGTH: 663
<212> TYPE: DNA
<213> ORGANISM: Arabidopsis thaliana

<400> SEQUENCE: 29

```
atgagggaa ggagctacac tccgtcacca cctaggggtt atgggaggag gggtcgaagc    60
ccaagcccta gaggccgata tggaggtcgt agcagggacc tcccgaccag tcttttggtt   120
cgcaatctac gccatgattg caggcaagaa gatctcagga agtcgtttga gcagtttggt   180
cctgtcaagg acatttacct gccaagggat tattataccg gagatccgcg agggtttggg   240
ttcgttcaat ttatggaccc tgctgatgct gctgatgcaa acatcacat  ggatggttat   300
cttcttcttg gccgtgagtt gactgtcgtg tttgcagaag agaacagaaa gaaaccgact   360
gaaatgagag caagggagcg tggtggagga agatttcggg atagaagacg tactccacct   420
cgttactact ctcgctctcg ttctcctccc cctcgacgtg gtagatctcg gtcacggagc   480
ggtgactatt attcctcctcc cctagaaga catcacccaa gatctatctc gcccagggaa   540
gagcgatatg atgggaggag gtcatactcg cgctcacctg cctctgatgg ctcaaggggt   600
cgcagtttaa ctccagtcag aggtaagagc cgcagcttaa ccccagccct agaagaagca   660
taa                                                                 663
```

<210> SEQ ID NO 30
<211> LENGTH: 220
<212> TYPE: PRT
<213> ORGANISM: Arabidopsis thaliana

<400> SEQUENCE: 30

```
Met Arg Gly Arg Ser Tyr Thr Pro Ser Pro Arg Gly Tyr Gly Arg
1               5                   10                  15

Arg Gly Arg Ser Pro Ser Pro Arg Gly Arg Tyr Gly Gly Arg Ser Arg
                20                  25                  30

Asp Leu Pro Thr Ser Leu Leu Val Arg Asn Leu Arg His Asp Cys Arg
            35                  40                  45

Gln Glu Asp Leu Arg Lys Ser Phe Glu Gln Phe Gly Pro Val Lys Asp
        50                  55                  60

Ile Tyr Leu Pro Arg Asp Tyr Tyr Thr Gly Asp Pro Arg Gly Phe Gly
65                  70                  75                  80

Phe Val Gln Phe Met Asp Pro Ala Asp Ala Ala Asp Ala Lys His His
                85                  90                  95

Met Asp Gly Tyr Leu Leu Leu Gly Arg Glu Leu Thr Val Val Phe Ala
            100                 105                 110

Glu Glu Asn Arg Lys Lys Pro Thr Glu Met Arg Ala Arg Glu Arg Gly
        115                 120                 125

Gly Gly Arg Phe Arg Asp Arg Arg Thr Pro Pro Arg Tyr Tyr Ser
    130                 135                 140

Arg Ser Arg Ser Pro Pro Pro Arg Gly Arg Ser Arg Ser Arg Ser
145                 150                 155                 160

Gly Asp Tyr Tyr Ser Pro Pro Arg His His Pro Arg Ser Ile
                165                 170                 175

Ser Pro Arg Glu Glu Arg Tyr Asp Gly Arg Ser Tyr Ser Arg Ser
            180                 185                 190

Pro Ala Ser Asp Gly Ser Arg Gly Arg Ser Leu Thr Pro Val Arg Gly
        195                 200                 205
```

Lys Ser Arg Ser Leu Thr Pro Ala Leu Glu Glu Ala
    210             215                 220

<210> SEQ ID NO 31
<211> LENGTH: 792
<212> TYPE: DNA
<213> ORGANISM: Arabidopsis thaliana

<400> SEQUENCE: 31 atgagggga ggagctacac tccgtcacca cctagggtt atgggaggag gggtcgaagc     60
ccaagcccta gaggccgata tggaggtcgt agcaggacc tcccgaccag tcttttggtt    120
cgcaatctac gccatgattg caggcaagaa gatctcagga agtcgtttga gcagtttggt    180
cctgtcaagg acatttacct gccaaggat tattataccg gagatccgcg agggttgg      240
ttcgttcaat ttatggaccc tgctgatgct gctgatgcaa acatcacat ggatggttat    300
cttcttcttg ccgtgagtt gactgtcgtg tttgcagaag agaacagaaa gaaaccgact    360
gaaatgagag caagggagcg tggtggagga agatttcggg atagaagacg tactccacct    420
cgttactact ctcgctctcg ttctcctccc cctcgacgtg gtagatctcg gtcacggagc    480
ggtgactatt attctcctcc ccctagaaga catcacccaa gatctatctc gcccagggaa    540
gagcgatatg atgggaggag gtcatactcg cgctcacctg cctctgatgg ctcaaggggt    600
cgcagtttaa ctccagtcag aggtaagagc cgcagcttaa gccccagccc tagaagaagc    660
ataagccgta gccctagaag aagcaggagt ccgaggagaa gcagaagaag ctacactcct    720
gaacccgcca gaagcaggag ccaaagcccg catgggggcc agtatgacga agaccgttca    780
ccaagccagt ga                                                       792

<210> SEQ ID NO 32
<211> LENGTH: 263
<212> TYPE: PRT
<213> ORGANISM: Arabidopsis thaliana

<400> SEQUENCE: 32

Met Arg Gly Arg Ser Tyr Thr Pro Ser Pro Arg Gly Tyr Gly Arg
1               5                   10                  15

Arg Gly Arg Ser Pro Ser Pro Arg Gly Arg Tyr Gly Gly Arg Ser Arg
            20                  25                  30

Asp Leu Pro Thr Ser Leu Leu Val Arg Asn Leu Arg His Asp Cys Arg
        35                  40                  45

Gln Glu Asp Leu Arg Lys Ser Phe Glu Gln Phe Gly Pro Val Lys Asp
    50                  55                  60

Ile Tyr Leu Pro Arg Asp Tyr Tyr Thr Gly Asp Pro Arg Gly Phe Gly
65                  70                  75                  80

Phe Val Gln Phe Met Asp Pro Ala Asp Ala Ala Asp Ala Lys His His
                85                  90                  95

Met Asp Gly Tyr Leu Leu Leu Gly Arg Glu Leu Thr Val Val Phe Ala
            100                 105                 110

Glu Glu Asn Arg Lys Lys Pro Thr Glu Met Arg Ala Arg Glu Arg Gly
        115                 120                 125

Gly Gly Arg Phe Arg Asp Arg Arg Arg Thr Pro Pro Arg Tyr Tyr Ser
    130                 135                 140

Arg Ser Arg Ser Pro Pro Pro Arg Arg Gly Ser Arg Ser Arg Ser
145                 150                 155                 160

Gly Asp Tyr Tyr Ser Pro Pro Pro Arg Arg His His Pro Arg Ser Ile
                165                 170                 175

Ser Pro Arg Glu Glu Arg Tyr Asp Gly Arg Ser Tyr Ser Arg Ser
        180                 185                 190

Pro Ala Ser Asp Gly Ser Arg Gly Arg Ser Leu Thr Pro Val Arg Gly
        195                 200                 205

Lys Ser Arg Ser Leu Ser Pro Ser Arg Arg Ser Ile Ser Arg Ser
        210                 215                 220

Pro Arg Arg Ser Arg Ser Pro Arg Arg Ser Arg Ser Tyr Thr Pro
225                 230                 235                 240

Glu Pro Ala Arg Ser Arg Ser Gln Ser Pro His Gly Gly Gln Tyr Asp
        245                 250                 255

Glu Asp Arg Ser Pro Ser Gln
        260

<210> SEQ ID NO 33
<211> LENGTH: 657
<212> TYPE: DNA
<213> ORGANISM: Oryza sativa

<400> SEQUENCE: 33

```
atgggaagag ctatgatta tggtccatca ccgccaagag aatacaggag aagagcccgc      60
agcccaagtc ctcgtgggcg ctatggaggc cgtgacaggg atctcccaac tagtcttttg    120
gtgaggaatc ttcgccgtga ctgtaggcct gatgatctac gaagaccatt tggaaaattt    180
ggtcgtgtca agatatata tcttccaaga gattattaca ctggggagcc tcgaggattt     240
gggttcatcc aatattatga tcctgaggat gctgctgatg caaaatacca catggatggg    300
caaattcttc ttggcaggga agttactgtt gtatttgctg aggagaacag aaagaaacca    360
tctgagatga gggctaggga agagtcggt agcaggacc gttcttatga tcgcaggtcg      420
cgctctccta gatactcccg ctcaaggtca cctgtgtact ctccaagatc acggtcccgt    480
agtcgaagct actcacctgc acctaagaga aagcactatt caagcaggtc tcctgcccgt    540
cgggagagat ctctgtcgcg ctcaccagcg acagcagat cacgaagtag aagcctctct     600
gatgaccgcc gcagcaagtc acctgacagg gagaggtctc tttctgttag ccggtga       657
```

<210> SEQ ID NO 34
<211> LENGTH: 218
<212> TYPE: PRT
<213> ORGANISM: Oryza sativa

<400> SEQUENCE: 34

Met Gly Arg Gly Tyr Asp Tyr Gly Pro Ser Pro Arg Glu Tyr Arg
1               5                   10                  15

Arg Arg Ala Arg Ser Pro Ser Pro Arg Gly Arg Tyr Gly Gly Arg Asp
        20                  25                  30

Arg Asp Leu Pro Thr Ser Leu Leu Val Arg Asn Leu Arg Arg Asp Cys
        35                  40                  45

Arg Pro Asp Asp Leu Arg Arg Pro Phe Gly Lys Phe Gly Arg Val Lys
    50                  55                  60

Asp Ile Tyr Leu Pro Arg Asp Tyr Tyr Thr Gly Glu Pro Arg Gly Phe
65                  70                  75                  80

Gly Phe Ile Gln Tyr Tyr Asp Pro Glu Asp Ala Ala Asp Ala Lys Tyr
            85                  90                  95

His Met Asp Gly Gln Ile Leu Leu Gly Arg Glu Val Thr Val Val Phe
            100                 105                 110

Ala Glu Glu Asn Arg Lys Lys Pro Ser Glu Met Arg Ala Arg Glu Arg
        115                 120                 125

Val Gly Ser Arg Asp Arg Ser Tyr Asp Arg Ser Arg Ser Pro Arg
    130                 135                 140

Tyr Ser Arg Ser Arg Ser Pro Val Tyr Ser Pro Arg Ser Arg Ser Arg
145                 150                 155                 160

Ser Arg Ser Tyr Ser Pro Ala Pro Lys Arg Lys His Tyr Ser Ser Arg
                165                 170                 175

Ser Pro Ala Arg Arg Glu Arg Ser Leu Ser Arg Ser Pro Ala Asp Ser
            180                 185                 190

Arg Ser Arg Ser Arg Ser Leu Ser Asp Asp Arg Ser Lys Ser Pro
        195                 200                 205

Asp Arg Glu Arg Ser Leu Ser Val Ser Arg
    210                 215

<210> SEQ ID NO 35
<211> LENGTH: 738
<212> TYPE: DNA
<213> ORGANISM: Vitis vinifera

<400> SEQUENCE: 35
atgaggggaa ggagttacag tccctcgcca ccaagggcct atggccgaag ggggcggagc     60
cctagcccaa gaggccgtta tggtggtcgt ggtagtgcta gagatctccc gactagtctt    120
ctagttcgca accttcgtca tgattgcagg ggtgaagacc ttcgaaggcc atttgggcag    180
tttggtcctc ttaaggatat ttacttgccc aggattatt atactgggga accgaggggc     240
tttggttttg tccaatatgt ggaccctgct gatgctgcag aagctaaata tcaaatggat    300
ggtcagattc ttcatggccg ggagttgact gttgtatttg cggaggagaa taggaagaaa    360
ccttctgata tgagggcaag agagcgtgga aggggtcgat ttatgatcg aagaaggtct     420 cccccttcgtt attcccgatc cccaccgcca cggcacgcaa gatctccgtc cgtggacgt     480 gattattatt ccccttcacc taagcggcga cagtactcaa ggtctgtttc cccacaagat    540
aggaggtaca gtcgagatag gtcatacacg cctgatggta ggaggaggtc gtacacccgt    600
tcaccaccct acaatggttc taggagccgc agccagagcc caataagggg tgaaagtccg    660
agcaggctcc aaagccgtag cccagatcct gaagattacc cacgagaagc agtgagagat    720
aggtctccca gtgagtga                                                   738

<210> SEQ ID NO 36
<211> LENGTH: 245
<212> TYPE: PRT
<213> ORGANISM: Vitis vinifera

<400> SEQUENCE: 36

Met Arg Gly Arg Ser Tyr Ser Pro Ser Pro Arg Ala Tyr Gly Arg
1               5                   10                  15

Arg Gly Arg Ser Pro Ser Pro Arg Gly Arg Tyr Gly Gly Arg Gly Ser
            20                  25                  30

Ala Arg Asp Leu Pro Thr Ser Leu Leu Val Arg Asn Leu Arg His Asp
        35                  40                  45

Cys Arg Gly Glu Asp Leu Arg Arg Pro Phe Gly Gln Phe Gly Pro Leu
    50                  55                  60

Lys Asp Ile Tyr Leu Pro Arg Asp Tyr Thr Gly Glu Pro Arg Gly
65                  70                  75                  80

Phe Gly Phe Val Gln Tyr Val Asp Pro Ala Asp Ala Ala Glu Ala Lys
                85                  90                  95

Tyr Gln Met Asp Gly Gln Ile Leu His Gly Arg Glu Leu Thr Val Val

```
              100                 105                 110
Phe Ala Glu Glu Asn Arg Lys Lys Pro Ser Asp Met Arg Ala Arg Glu
            115                 120                 125

Arg Gly Arg Gly Arg Phe Tyr Asp Arg Arg Ser Pro Leu Arg Tyr
        130                 135                 140

Ser Arg Ser Pro Pro Arg His Ala Arg Ser Pro Ser Arg Gly Arg
145                 150                 155                 160

Asp Tyr Tyr Ser Pro Ser Pro Lys Arg Arg Gln Tyr Ser Arg Ser Val
                165                 170                 175

Ser Pro Gln Asp Arg Arg Tyr Ser Arg Asp Arg Ser Tyr Thr Pro Asp
            180                 185                 190

Gly Arg Arg Arg Ser Tyr Thr Arg Ser Pro Pro Tyr Asn Gly Ser Arg
                195                 200                 205

Ser Arg Ser Gln Ser Pro Ile Arg Gly Glu Ser Pro Ser Arg Leu Gln
            210                 215                 220

Ser Arg Ser Pro Asp Pro Glu Asp Tyr Pro Arg Glu Ala Val Arg Asp
225                 230                 235                 240

Arg Ser Pro Ser Glu
            245

<210> SEQ ID NO 37
<211> LENGTH: 681
<212> TYPE: DNA
<213> ORGANISM: Glycine max

<400> SEQUENCE: 37
atgaacattt tcaaatcccc actggaccat gatttgaact gtggtggaat attccacgac      60
tcagcagaag catcttattc gtctgaaaca aggagcaccc cctcagacga agaagtgatt     120
ctagcgtcag cgcggccaaa gaagcgagcg ggaagaagag tcttcaagga acaaggcac     180
cccgtctacc gaggagtgcg tcgcaggaac aagaacaagt gggtctgcga gatgcgagtc     240
cccaacaaca actcacggat ttggctcggg acatacccaa cgcccgaaat ggccgcacgt     300
gcgcacgacg ttgcggcgct cgcgctcagg ggaaagtccg cgtgcctcaa cttcgcggac     360
tccaggtggc ggctgacggt gccggcgacc accaacgcgg aggagatacg gcgagcggcg     420
ggggaggctg ctgaggcatt tgcagttgca gatggggacg acgttaatat tgaccaacag     480
cagagtgtga tggccacgaa tgatgatgaa gttcaagagc tctccagca ggaggaggtt     540
caagacttgc atgatttgct tttgagtatt gcgaatgagc ctttgatgtc tcctccaccc     600
tgtgcaagag atggtaggga ctggaatgac gtggacatat tgatgatga tgaaatctca     660
ctgtggaact tctcaatttg a                                              681

<210> SEQ ID NO 38
<211> LENGTH: 226
<212> TYPE: PRT
<213> ORGANISM: Glycine max

<400> SEQUENCE: 38

Met Asn Ile Phe Lys Ser Pro Leu Asp His Asp Leu Asn Cys Gly Gly
1               5                   10                  15

Ile Phe His Asp Ser Ala Glu Ala Ser Tyr Ser Ser Glu Thr Arg Ser
            20                  25                  30

Thr Pro Ser Asp Glu Glu Val Ile Leu Ala Ser Ala Arg Pro Lys Lys
        35                  40                  45

Arg Ala Gly Arg Arg Val Phe Lys Glu Thr Arg His Pro Val Tyr Arg
    50                  55                  60
```

Gly Val Arg Arg Arg Asn Lys Asn Lys Trp Val Cys Glu Met Arg Val
65                  70                  75                  80

Pro Asn Asn Asn Ser Arg Ile Trp Leu Gly Thr Tyr Pro Thr Pro Glu
            85                  90                  95

Met Ala Ala Arg Ala His Asp Val Ala Leu Ala Leu Arg Gly Lys
        100                 105                 110

Ser Ala Cys Leu Asn Phe Ala Asp Ser Arg Trp Arg Leu Thr Val Pro
        115                 120                 125

Ala Thr Thr Asn Ala Glu Glu Ile Arg Arg Ala Ala Gly Glu Ala Ala
        130                 135                 140

Glu Ala Phe Ala Val Ala Asp Gly Asp Val Asn Ile Asp Gln Gln
145                 150                 155                 160

Gln Ser Val Met Ala Thr Asn Asp Asp Glu Val Gln Gly Pro Leu Gln
                165                 170                 175

Gln Glu Glu Val Gln Asp Leu His Asp Leu Leu Leu Ser Ile Ala Asn
            180                 185                 190

Glu Pro Leu Met Ser Pro Pro Pro Cys Ala Arg Asp Gly Arg Asp Trp
        195                 200                 205

Asn Asp Val Asp Ile Phe Asp Asp Asp Glu Ile Ser Leu Trp Asn Phe
210                 215                 220

Ser Ile
225

<210> SEQ ID NO 39
<211> LENGTH: 696
<212> TYPE: DNA
<213> ORGANISM: Glycine max

<400> SEQUENCE: 39
atggacatga attcctcagg tggtgcctgc ggttggcttt atgattatgg ctttgatatc      60
cctgttgctg gttctgactt catggcttca gactctggtg gtttcagttg ggggccccag     120
agttacaact tcaagggtcc ttcaaatatg agcttggaaa tggaatactc actggattca     180
actgtcatgg aaaatggtcc ttcaaagcgg ttaaggacta atcatgtgc atctggctcc      240
aaggcatgtc gtgagaaatt gcgaagggat aaacttaatg agaggtttct ggaattgagt     300
tcgatcttgg agcctggtag acagcccaaa acagacaaag ttgcattatt aagcgatgcg     360
gctcgagtgg taatccaatt gagaaatgaa gccgagaggc tgaaggaaat gaatgatgaa     420
ttacaggcaa agttaaagga ttgaagggt gagaagaatg agcttcgtga tgagaagaat     480
aggctgaagg aagagaaaga aaagttggag aagcaagtga aactgacaaa tatacaaccc     540
agcttcctac ctcaagcccc agatgctaaa gggcaagttg gtagccacaa gctgataccct    600
ttcattggat accctggaat tgccatgtgg cagtttatgt cccctgctgc agttgatact     660
tcaaaggatc atctgcttcg acctccagtt gcataa                               696

<210> SEQ ID NO 40
<211> LENGTH: 231
<212> TYPE: PRT
<213> ORGANISM: Glycine max

<400> SEQUENCE: 40

Met Asp Met Asn Ser Ser Gly Gly Ala Cys Gly Trp Leu Tyr Asp Tyr
1               5                   10                  15

Gly Phe Asp Ile Pro Val Ala Gly Ser Asp Phe Met Ala Ser Asp Ser
            20                  25                  30

```
Gly Gly Phe Ser Trp Gly Pro Gln Ser Tyr Asn Phe Lys Gly Pro Ser
        35                  40                  45

Asn Met Ser Leu Glu Met Glu Tyr Ser Leu Asp Ser Thr Val Met Glu
 50                  55                  60

Asn Gly Pro Ser Lys Arg Leu Arg Thr Glu Ser Cys Ala Ser Gly Ser
 65                  70                  75                  80

Lys Ala Cys Arg Glu Lys Leu Arg Arg Asp Lys Leu Asn Glu Arg Phe
                 85                  90                  95

Leu Glu Leu Ser Ser Ile Leu Glu Pro Gly Arg Gln Pro Lys Thr Asp
            100                 105                 110

Lys Val Ala Leu Leu Ser Asp Ala Ala Arg Val Val Ile Gln Leu Arg
        115                 120                 125

Asn Glu Ala Glu Arg Leu Lys Glu Met Asn Asp Glu Leu Gln Ala Lys
130                 135                 140

Val Lys Glu Leu Lys Gly Glu Lys Asn Glu Leu Arg Asp Glu Lys Asn
145                 150                 155                 160

Arg Leu Lys Glu Glu Lys Lys Leu Glu Lys Gln Val Lys Leu Thr
                165                 170                 175

Asn Ile Gln Pro Ser Phe Leu Pro Gln Ala Pro Asp Ala Lys Gly Gln
            180                 185                 190

Val Gly Ser His Lys Leu Ile Pro Phe Ile Gly Tyr Pro Gly Ile Ala
        195                 200                 205

Met Trp Gln Phe Met Ser Pro Ala Ala Val Asp Thr Ser Lys Asp His
210                 215                 220

Leu Leu Arg Pro Pro Val Ala
225                 230

<210> SEQ ID NO 41
<211> LENGTH: 679
<212> TYPE: DNA
<213> ORGANISM: Lotus japonicus

<400> SEQUENCE: 41
atggaaattg attcctcagg tgattcctgt tggctctatg attatggctt tgatgatatc      60
tctgttgctg ctgcagctga tttcatggtt gcagactctg ctgatttcac ctgggttcct     120
tccaatatga acttgaaat ggaatactca ctggattcaa ctgtcttcga agtggccct      180
tcaaagcggt taaggactga atcaagtgtg tctggctcca aggcatgtcg tgagaaacta     240
cgaagggata aactgaatga gaggtttctg gaattgagtt ctatcttgga gcctggtagg     300
cagcccaaaa cagacaaggc tgctataata agtgacgcgg ttcgagtggt aacccaatta     360
agaaatgaag ctgagaagct gaaggaaatg aataacgatt tacaagaaaa aattaaagag     420
ttgaaggctg agaagaatga gattcgtgat gagaagaata gctgaagct agacaaagaa      480
aagttagaga agaaggtcaa attgagaaat gtacagcctg cttcctccc tcacgccgac      540
gcagctgtta aagggaaagg tgctgctagc cacaagctga taccttacat tggttatcct     600
ggaattgcca tgtggcagtt tatgccctct gctgtacttg atacatcaag ggatcatctt     660
cttcgacctc cagttgcct                                                  679

<210> SEQ ID NO 42
<211> LENGTH: 226
<212> TYPE: PRT
<213> ORGANISM: Lotus japonicus

<400> SEQUENCE: 42

Met Glu Ile Asp Ser Ser Gly Asp Ser Cys Trp Leu Tyr Asp Tyr Gly
```

```
                1               5                  10                 15
Phe Asp Asp Ile Ser Val Ala Ala Ala Asp Phe Met Val Ala Asp
                    20                  25                  30

Ser Ala Asp Phe Thr Trp Val Pro Ser Asn Met Asn Leu Glu Met Glu
                35                  40                  45

Tyr Ser Leu Asp Ser Thr Val Phe Glu Ser Gly Pro Ser Lys Arg Leu
            50                  55                  60

Arg Thr Glu Ser Ser Val Ser Gly Ser Lys Ala Cys Arg Glu Lys Leu
65                  70                  75                  80

Arg Arg Asp Lys Leu Asn Glu Arg Phe Leu Glu Leu Ser Ser Ile Leu
                85                  90                  95

Glu Pro Gly Arg Gln Pro Lys Thr Asp Lys Ala Ala Ile Ile Ser Asp
                100                 105                 110

Ala Val Arg Val Val Thr Gln Leu Arg Asn Glu Ala Glu Lys Leu Lys
            115                 120                 125

Glu Met Asn Asn Asp Leu Gln Glu Lys Ile Lys Glu Leu Lys Ala Glu
            130                 135                 140

Lys Asn Glu Ile Arg Asp Glu Lys Asn Lys Leu Lys Leu Asp Lys Glu
145                 150                 155                 160

Lys Leu Glu Lys Lys Val Lys Leu Arg Asn Val Gln Pro Gly Phe Leu
                165                 170                 175

Pro His Ala Asp Ala Ala Val Lys Gly Lys Gly Ala Ala Ser His Lys
            180                 185                 190

Leu Ile Pro Tyr Ile Gly Tyr Pro Gly Ile Ala Met Trp Gln Phe Met
            195                 200                 205

Pro Ser Ala Val Leu Asp Thr Ser Arg Asp His Leu Leu Arg Pro Pro
            210                 215                 220

Val Ala
225

<210> SEQ ID NO 43
<211> LENGTH: 699
<212> TYPE: DNA
<213> ORGANISM: Vigna unguiculata

<400> SEQUENCE: 43
atggacatga attcctcaag tggtgcctcc ggttggcttt atgattatgg ttttgatatc      60
cctgttgctg gtgctgactt catggttgca gcagactctg gaggttttag ttgggggcct     120
caaaatcaca ccttgaaggg tccttcacat acgagcttgg aaatggaata ctcactggat     180
tcaactgttc tggaaaatag tccttcaaag cggttaagga ctgagtcatg tgcatctggc     240
gccaaggcgt gtcgcgaaaa aatgcgaagg ataaactga atgataggtt ctctggaattg     300 agttccatct tggagcctgg taggccgccc aaaacagaca agttgcaat attaagtgat     360 gctgctcgag tggtagtcca attgagaaat gaaccgaga ggcttaagga atgaatgat     420 gaactacagg gaaaagttaa agaattgaag gctgagaaga atgagcttcg tgatgagaag     480
aatatgctga aggatgagaa agaaaagttg gagcaacagg taaaactgac aaatatacat     540
aacagtttcg tccctcaagc ccaagctgct aaaggacaag ttggtagcca caagctgata     600
cctttcattg ctatcctgg aattgctatg tggcagttta tgcctcctgc tgcagttgat     660
acatcaaagg atcatctgct tcgacctcca gttgcataa                            699

<210> SEQ ID NO 44
<211> LENGTH: 232
<212> TYPE: PRT
```

<213> ORGANISM: Vigna unguiculata

<400> SEQUENCE: 44

```
Met Asp Met Asn Ser Ser Gly Ala Ser Gly Trp Leu Tyr Asp Tyr
1               5                   10                  15

Gly Phe Asp Ile Pro Val Ala Gly Ala Asp Phe Met Val Ala Ala Asp
            20                  25                  30

Ser Gly Gly Phe Ser Trp Gly Pro Gln Asn His Thr Leu Lys Gly Pro
        35                  40                  45

Ser His Thr Ser Leu Glu Met Glu Tyr Ser Leu Asp Ser Thr Val Leu
    50                  55                  60

Glu Asn Ser Pro Ser Lys Arg Leu Arg Thr Glu Ser Cys Ala Ser Gly
65                  70                  75                  80

Ala Lys Ala Cys Arg Glu Lys Met Arg Arg Asp Lys Leu Asn Asp Arg
                85                  90                  95

Phe Leu Glu Leu Ser Ser Ile Leu Glu Pro Gly Arg Pro Pro Lys Thr
            100                 105                 110

Asp Lys Val Ala Ile Leu Ser Asp Ala Ala Arg Val Val Gln Leu
        115                 120                 125

Arg Asn Glu Thr Glu Arg Leu Lys Glu Met Asn Asp Glu Leu Gln Gly
    130                 135                 140

Lys Val Lys Glu Leu Lys Ala Glu Lys Asn Glu Leu Arg Asp Glu Lys
145                 150                 155                 160

Asn Met Leu Lys Asp Glu Lys Glu Lys Leu Glu Gln Gln Val Lys Leu
                165                 170                 175

Thr Asn Ile His Asn Ser Phe Val Pro Gln Ala Gln Ala Ala Lys Gly
            180                 185                 190

Gln Val Gly Ser His Lys Leu Ile Pro Phe Ile Gly Tyr Pro Gly Ile
        195                 200                 205

Ala Met Trp Gln Phe Met Pro Pro Ala Ala Val Asp Thr Ser Lys Asp
    210                 215                 220

His Leu Leu Arg Pro Pro Val Ala
225                 230
```

<210> SEQ ID NO 45
<211> LENGTH: 702
<212> TYPE: DNA
<213> ORGANISM: Unknown
<220> FEATURE:
<223> OTHER INFORMATION: Synthetic sequence

<400> SEQUENCE: 45

```
atggacatga attcctcaag tggtgcctcc ggttggcttt atgattatgg ctttgatatc    60
cctgttgctg gtgctgactt catggctgca gcagactctg gaggttttag ttggggccct   120
caaaatcaca ccttaaaggc tccttcaaat acaagcttgg atatggaata ctcactggat   180
tcaactgtcc tggaaaatgg tccttcaaag cggttaagga ctgagtcatg tgcatctggc   240
gccaaggcat gtcgcgaaaa attgcgaagg ataaactga atgagaggtt tctggaattg   300
agttccatct ggagcctggt taggccgccc aaaacagaca agttgtaat attaagtgat   360 gctgttcgag cggtagtcca attgagaaat gaagccgaga ggcttaagga aatgaacgat   420
gaattacagg gaaagttaa agaattgaag gctgagaaga atgagcttcg tgatgagaag   480
aatatgctga aggaagagaa agaaaagttg agcaacagg taaaactgac aaatgttatg   540
cggcacagct cctgcctca gccccagct gctaaagaac aagttggtag ccacaagctg   600 ataccttttca ttggctatcc tggaattgct atgtggcagt ttatgccccc tgctgcagtg   660
```
gatacatcaa aggatcatct gcttcgacct ccagttgcat aa        702

<210> SEQ ID NO 46
<211> LENGTH: 233
<212> TYPE: PRT
<213> ORGANISM: Unknown
<220> FEATURE:
<223> OTHER INFORMATION: Synthetic sequence

<400> SEQUENCE: 46

Met Asp Met Asn Ser Ser Gly Ala Ser Gly Trp Leu Tyr Asp Tyr
1               5                   10                  15

Gly Phe Asp Ile Pro Val Ala Gly Ala Asp Phe Met Ala Ala Asp
                20                  25                  30

Ser Gly Gly Phe Ser Trp Gly Pro Gln Asn His Thr Leu Lys Ala Pro
            35                  40                  45

Ser Asn Thr Ser Leu Asp Met Glu Tyr Ser Leu Asp Ser Thr Val Leu
        50                  55                  60

Glu Asn Gly Pro Ser Lys Arg Leu Arg Thr Glu Ser Cys Ala Ser Gly
65                  70                  75                  80

Ala Lys Ala Cys Arg Glu Lys Leu Arg Arg Asp Lys Leu Asn Glu Arg
                85                  90                  95

Phe Leu Glu Leu Ser Ser Ile Leu Glu Pro Gly Arg Pro Pro Lys Thr
            100                 105                 110

Asp Lys Val Val Ile Leu Ser Asp Ala Val Arg Ala Val Gln Leu
        115                 120                 125

Arg Asn Glu Ala Glu Arg Leu Lys Glu Met Asn Asp Glu Leu Gln Gly
130                 135                 140

Lys Val Lys Glu Leu Lys Ala Glu Lys Asn Glu Leu Arg Asp Glu Lys
145                 150                 155                 160

Asn Met Leu Lys Glu Glu Lys Glu Lys Leu Glu Gln Gln Val Lys Leu
                165                 170                 175

Thr Asn Val Met Arg His Ser Phe Leu Pro Gln Ala Pro Ala Ala Lys
            180                 185                 190

Glu Gln Val Gly Ser His Lys Leu Ile Pro Phe Ile Gly Tyr Pro Gly
        195                 200                 205

Ile Ala Met Trp Gln Phe Met Pro Pro Ala Ala Val Asp Thr Ser Lys
210                 215                 220

Asp His Leu Leu Arg Pro Pro Val Ala
225                 230

<210> SEQ ID NO 47
<211> LENGTH: 783
<212> TYPE: DNA
<213> ORGANISM: Medicago truncatula

<400> SEQUENCE: 47
atggatatgg attcaacagg tggttcctcc atttggctct atgattatgg ctatgatgat        60
atatctattt ctgctgctga tttcatggct tctgactctt ctgctgctgc ttctactttc       120
acctggatgc ctcagcctca gtctcagact cagatcatca atcctccttc ctcccatatg       180
agcttggaaa tggattactc cctggattca actgtaatgg aaagtaaccc ttcaaagcgc       240
atggaaatgg aatactcact ggattcaaca gtactggaaa acggcccttc aaagcggtta       300
aggacagaat catatgcatc tagctccaag gcaggtcgtg agaaagtgcg aagggataaa       360
ttgaatgaca ggtttatgga attgagttct gtcttagagc ctgatacact gcccaaaaca       420

```
gacaaggtta gcctattaaa tgacgcggtt cgagtggtga cccaattaag aaatgaagct    480
gagaggctca aggaaggaa tgatgaattg cgcgaaaaag ttaaagaact taaggccgag     540
aagaaagagc ttcgtgatga gaaaaataag ctgaagctag acaaagaaaa gttggaacag    600
caagtcaaat tagcaagtgt acagtccaac ttcctctcta atgcaatggc tgctaaagga    660
caaactgcta accacaagct gatgcctttc attggttatc ctggaatttc aatgtggcag    720
tttatgtcac tgctacagt tgatacatca caggatcatc tgcttcgacc tccagttgct    780
taa                                                                 783
```

```
<210> SEQ ID NO 48
<211> LENGTH: 260
<212> TYPE: PRT
<213> ORGANISM: Medicago truncatula

<400> SEQUENCE: 48

Met Asp Met Asp Ser Thr Gly Gly Ser Ser Ile Trp Leu Tyr Asp Tyr
1               5                   10                  15

Gly Tyr Asp Asp Ile Ser Ile Ser Ala Ala Asp Phe Met Ala Ser Asp
            20                  25                  30

Ser Ser Ala Ala Ala Ser Thr Phe Thr Trp Met Pro Gln Pro Gln Ser
        35                  40                  45

Gln Thr Gln Ile Ile Asn Pro Pro Ser Ser His Met Ser Leu Glu Met
    50                  55                  60

Asp Tyr Ser Leu Asp Ser Thr Val Met Glu Ser Asn Pro Ser Lys Arg
65                  70                  75                  80

Met Glu Met Glu Tyr Ser Leu Asp Ser Thr Val Leu Glu Asn Gly Pro
                85                  90                  95

Ser Lys Arg Leu Arg Thr Glu Ser Tyr Ala Ser Ser Lys Ala Gly
            100                 105                 110

Arg Glu Lys Val Arg Arg Asp Lys Leu Asn Asp Arg Phe Met Glu Leu
        115                 120                 125

Ser Ser Val Leu Glu Pro Asp Thr Leu Pro Lys Thr Asp Lys Val Ser
    130                 135                 140

Leu Leu Asn Asp Ala Val Arg Val Val Thr Gln Leu Arg Asn Glu Ala
145                 150                 155                 160

Glu Arg Leu Lys Glu Arg Asn Asp Glu Leu Arg Glu Lys Val Lys Glu
                165                 170                 175

Leu Lys Ala Glu Lys Lys Glu Leu Arg Asp Glu Lys Asn Lys Leu Lys
            180                 185                 190

Leu Asp Lys Glu Lys Leu Glu Gln Gln Val Lys Leu Ala Ser Val Gln
        195                 200                 205

Ser Asn Phe Leu Ser Asn Ala Met Ala Ala Lys Gly Gln Thr Ala Asn
    210                 215                 220

His Lys Leu Met Pro Phe Ile Gly Tyr Pro Gly Ile Ser Met Trp Gln
225                 230                 235                 240

Phe Met Ser Pro Ala Thr Val Asp Thr Ser Gln Asp His Leu Leu Arg
                245                 250                 255

Pro Pro Val Ala
            260

<210> SEQ ID NO 49
<211> LENGTH: 576
<212> TYPE: DNA
<213> ORGANISM: Glycine max

<400> SEQUENCE: 49
```

```
atgggcacca aactatttca cacattgctc ctcctctctt acgccctctc caatgtcata      60
ggagaagaaa caggcttcgt gggcacacta cccccaaat ccttaggtct tcacaagaaa      120
caaaccctaa gccacttcaa attctactgg cacgacatag tgagcagtgg agccaactcc     180
acctcagcca cagtcatccc accactcccc aaatacaaca caagcacttc cttcggcatg     240
gttaacgtga tggacaaccc cttgacgttg ggccccgaga tgggctccaa gctcgtgggc     300
cgggccgagg ggttctacgc actaacatca caatcccaga tcaatttgct catggtcatg     360
aactttgcct tgtttgaagg aagtacaac gggagcacca taactatcgt ggggaggaac      420
gctgttagtg aaaatgaaaa ggatattcct gtggttggtg ggagtgggat tttttaagttt    480 gctaagggat atgctcatgc caagacctac ttctttgatc ccaagactgg ggatgctacc     540
actgagtaca acgtttatgt cctccataac gagtaa                               576
```

<210> SEQ ID NO 50
<211> LENGTH: 191
<212> TYPE: PRT
<213> ORGANISM: Glycine max

<400> SEQUENCE: 50

```
Met Gly Thr Lys Leu Phe His Thr Leu Leu Leu Ser Tyr Ala Leu
1               5                   10                  15

Ser Asn Val Ile Gly Glu Glu Thr Gly Phe Val Gly Thr Leu His Pro
            20                  25                  30

Lys Ser Leu Gly Leu His Lys Lys Gln Thr Leu Ser His Phe Lys Phe
        35                  40                  45

Tyr Trp His Asp Ile Val Ser Ser Gly Ala Asn Ser Thr Ser Ala Thr
    50                  55                  60

Val Ile Pro Pro Leu Pro Lys Tyr Asn Thr Ser Thr Ser Phe Gly Met
65                  70                  75                  80

Val Asn Val Met Asp Asn Pro Leu Thr Leu Gly Pro Glu Met Gly Ser
                85                  90                  95

Lys Leu Val Gly Arg Ala Glu Gly Phe Tyr Ala Leu Thr Ser Gln Ser
            100                 105                 110

Gln Ile Asn Leu Leu Met Val Met Asn Phe Ala Leu Phe Glu Gly Lys
        115                 120                 125

Tyr Asn Gly Ser Thr Ile Thr Ile Val Gly Arg Asn Ala Val Ser Glu
    130                 135                 140

Asn Glu Lys Asp Ile Pro Val Val Gly Gly Ser Gly Ile Phe Lys Phe
145                 150                 155                 160

Ala Lys Gly Tyr Ala His Ala Lys Thr Tyr Phe Phe Asp Pro Lys Thr
                165                 170                 175

Gly Asp Ala Thr Thr Glu Tyr Asn Val Tyr Val Leu His Asn Glu
            180                 185                 190
```

<210> SEQ ID NO 51
<211> LENGTH: 576
<212> TYPE: DNA
<213> ORGANISM: Glycine max

<400> SEQUENCE: 51

```
atgtccacca aactactcct aaccctaatc ctcatctctt acaccctctc caatgtcata      60
ggagaagaaa caggctttgt gggcacacta cccccaaat ccttaggtct tcacaagaaa      120
caaaccctaa gccacttcaa attctactgg catgacatag tgagcagtgg agccaactcc     180
acctcagcca caatcatccc accactcccc aaatacaaca caaccacttc cttcggcatg     240
```

```
gtcaacgtca tggacaaccc cttgactctg ggccccgagc tgggctccaa gctcgtgggc    300
cgggccgagg ggttctatgc cctaacctca cagtcccaga tcaacttgct tatggtcatg    360
aactttgcct tgtttgaagg aagtacaac gggagcacca taactatcgt ggggaggaac    420
gctgttagtg aaaatgaaaa ggatattcct gtggttggtg gaagtggggt ttttaagttt    480
gctaaaggct atgctcatgc caagacctac ttctttgatc ccaagactgg ggatgctacc    540
actgagtaca acatctatgt ccttcattac gagtaa                              576
```

<210> SEQ ID NO 52
<211> LENGTH: 191
<212> TYPE: PRT
<213> ORGANISM: Glycine max
<400> SEQUENCE: 52

```
Met Ser Thr Lys Leu Leu Leu Thr Leu Ile Leu Ile Ser Tyr Thr Leu
1               5                   10                  15

Ser Asn Val Ile Gly Glu Glu Thr Gly Phe Val Gly Thr Leu His Pro
                20                  25                  30

Lys Ser Leu Gly Leu His Lys Lys Gln Thr Leu Ser His Phe Lys Phe
            35                  40                  45

Tyr Trp His Asp Ile Val Ser Ser Gly Ala Asn Ser Thr Ser Ala Thr
    50                  55                  60

Ile Ile Pro Pro Leu Pro Lys Tyr Asn Thr Thr Ser Phe Gly Met
65                  70                  75                  80

Val Asn Val Met Asp Asn Pro Leu Thr Leu Gly Pro Glu Leu Gly Ser
                85                  90                  95

Lys Leu Val Gly Arg Ala Glu Gly Phe Tyr Ala Leu Thr Ser Gln Ser
            100                 105                 110

Gln Ile Asn Leu Leu Met Val Met Asn Phe Ala Leu Phe Glu Gly Lys
        115                 120                 125

Tyr Asn Gly Ser Thr Ile Thr Ile Val Gly Arg Asn Ala Val Ser Glu
    130                 135                 140

Asn Glu Lys Asp Ile Pro Val Val Gly Gly Ser Gly Val Phe Lys Phe
145                 150                 155                 160

Ala Lys Gly Tyr Ala His Ala Lys Thr Tyr Phe Phe Asp Pro Lys Thr
                165                 170                 175

Gly Asp Ala Thr Thr Glu Tyr Asn Ile Tyr Val Leu His Tyr Glu
            180                 185                 190
```

<210> SEQ ID NO 53
<211> LENGTH: 570
<212> TYPE: DNA
<213> ORGANISM: Vigna unguiculata
<400> SEQUENCE: 53

```
atggccaccc aattgctcct cacactgttc cttctctcct tcaccgtcgc caccatccaa     60
gcagaagaca ccggctacgt gggcacagtg gatcccaaat cccttggcct caacaagaaa    120 aaaccctaa gccactttag actctactgg caggacgtca tcagcggctc caacgccacc    180
gccataaaca tcatcccggc aatccccaag tacaacacca ccacctcctt cggctccgtc    240
accgtcaccg acaacgccct gaccgtcgga cccgaactca gctccaaggt tgtgggaaga    300
tccgaaggaa tctacgccct gacgtcgcag tcgcaggtta ctctcctcat ggtgatgaac    360
ttcgtcttga cggaaggaaa gtacaacggg agcagcttaa ctatcgtggg gaggaacgtg    420
gcttacgatg aacagaaaga gttgcctgtg gttggtggaa gtggggtttt caagtttgct    480
```

```
acaggttacg ctcatgctaa gacctatcac tttgaccctc ccaccggtga tgctaccact    540
gagtacaaca tctacgtctt ccattattga                                     570
```

<210> SEQ ID NO 54
<211> LENGTH: 189
<212> TYPE: PRT
<213> ORGANISM: Vigna unguiculata

<400> SEQUENCE: 54

```
Met Ala Thr Gln Leu Leu Thr Leu Phe Leu Leu Ser Phe Thr Val
1               5                   10                  15

Ala Thr Ile Gln Ala Glu Asp Thr Gly Tyr Val Gly Thr Val Asp Pro
            20                  25                  30

Lys Ser Leu Gly Leu Asn Lys Lys Thr Leu Ser His Phe Arg Leu
        35                  40                  45

Tyr Trp Gln Asp Val Ile Ser Gly Ser Asn Ala Thr Ala Ile Asn Ile
50                  55                  60

Ile Pro Ala Ile Pro Lys Tyr Asn Thr Thr Thr Ser Phe Gly Ser Val
65                  70                  75                  80

Thr Val Thr Asp Asn Ala Leu Thr Val Gly Pro Glu Leu Ser Ser Lys
                85                  90                  95

Val Val Gly Arg Ser Glu Gly Ile Tyr Ala Leu Thr Ser Gln Ser Gln
            100                 105                 110

Val Thr Leu Leu Met Val Met Asn Phe Val Leu Thr Glu Gly Lys Tyr
        115                 120                 125

Asn Gly Ser Ser Leu Thr Ile Val Gly Arg Asn Val Ala Tyr Asp Glu
130                 135                 140

Gln Lys Glu Leu Pro Val Val Gly Gly Ser Gly Val Phe Lys Phe Ala
145                 150                 155                 160

Thr Gly Tyr Ala His Ala Lys Thr Tyr His Phe Asp Pro Thr Gly
            165                 170                 175

Asp Ala Thr Thr Glu Tyr Asn Ile Tyr Val Phe His Tyr
        180                 185
```

<210> SEQ ID NO 55
<211> LENGTH: 570
<212> TYPE: DNA
<213> ORGANISM: Unknown
<220> FEATURE:
<223> OTHER INFORMATION: Synthetic sequence

<400> SEQUENCE: 55

```
atggccaccc aactgctcct cacgctgttc cttctctctt tcaccctcac caccatcaaa    60
gcagaagaca ctggcttcgt gggcacagtg gatcccaaat ccctaggcct caacaagaaa   120
caaaccctaa gccacttcag attctactgg cacgacatca taagcggctc caacgccaca   180
gccgtagaga tcatcgagcc acttcccaag tacaacacca ccacctcctt cggctccgtc   240
accgtgacgg acaacgcctt gaccctggga cccgaactga gctccaaggt ggtgggaaga   300
tccgaaggaa tctacgccct gacgtcgcag tcgcaggtta ctctgctcat ggtgatgaac   360
tttgtcttgt cggaagggaa gtacaacggg agcgccataa ctatcgtggg gaggaacgtg   420
gcctatgaag aagccaaaga gttgcctgtg attggtggaa gtggggtttt caagtttgct   480
acagggtatg ctaaggcaaa gacctactac tttgacccca aaactggtga tgctaccact   540
gagtacaaca tctatgtttt ccattactga                                    570
```

```
<210> SEQ ID NO 56
<211> LENGTH: 189
<212> TYPE: PRT
<213> ORGANISM: Unknown
<220> FEATURE:
<223> OTHER INFORMATION: Synthetic sequence

<400> SEQUENCE: 56

Met Ala Thr Gln Leu Leu Thr Leu Phe Leu Leu Ser Phe Thr Leu
1               5                   10                  15

Thr Thr Ile Lys Ala Glu Asp Thr Gly Phe Val Gly Thr Val Asp Pro
            20                  25                  30

Lys Ser Leu Gly Leu Asn Lys Lys Gln Thr Leu Ser His Phe Arg Phe
            35                  40                  45

Tyr Trp His Asp Ile Ile Ser Gly Ser Asn Ala Thr Ala Val Glu Ile
    50                  55                  60

Ile Glu Pro Leu Pro Lys Tyr Asn Thr Thr Thr Ser Phe Gly Ser Val
65              70                  75                  80

Thr Val Thr Asp Asn Ala Leu Thr Leu Gly Pro Glu Leu Ser Ser Lys
                85                  90                  95

Val Val Gly Arg Ser Glu Gly Ile Tyr Ala Leu Thr Ser Gln Ser Gln
            100                 105                 110

Val Thr Leu Leu Met Val Met Asn Phe Val Leu Ser Glu Gly Lys Tyr
        115                 120                 125

Asn Gly Ser Ala Ile Thr Ile Val Gly Arg Asn Val Ala Tyr Glu Glu
    130                 135                 140

Ala Lys Glu Leu Pro Val Ile Gly Gly Ser Gly Val Phe Lys Phe Ala
145                 150                 155                 160

Thr Gly Tyr Ala Lys Ala Lys Thr Tyr Tyr Phe Asp Pro Lys Thr Gly
                165                 170                 175

Asp Ala Thr Thr Glu Tyr Asn Ile Tyr Val Phe His Tyr
            180                 185

<210> SEQ ID NO 57
<211> LENGTH: 1999
<212> TYPE: DNA
<213> ORGANISM: Arabidopsis thaliana
<220> FEATURE:
<221> NAME/KEY: promoter
<222> LOCATION: (1)..(1999)

<400> SEQUENCE: 57
gtagtgccct tcatggatac caaaagagaa aatttgattt agtgcataca tataacaata      60
taacgccgca taataatact gtataaaaca gtcatgtaac gatatgacag cagtaataca     120
gttccaagag acgttataat cgtatgcaat catatgcttg cgtagatttt ccaacagttt     180
tgtttcgttg ataggaggaa ctcaacactc tagggtagtg attggtagac actattagca     240
caaaaaatat taattttact ctgatgttta ccaaaaaagt taccaatcaa atatttaaga     300
gatcgtactc ttccacggcg actctaaaaa ccaaagatat aggttagact cataactact     360
ttataaagaa aatgtttaac gataactacc gagatctaat aaataaacct tcattttcaa     420
gtatattata tttgcttctt tgtttatat atcaaaccaa gttctggttt ataaaaatat     480
tagataaaac tcgtctaaat aggtaggtgt aaaataaaat tttaaatttt tatcgataat     540
atttaaaatt tgaaaagtta ataatgatcc acacattttt tctaatattt aatttagtaa     600 ttttttgtatt aaataaaatt tcaatcatat acattcgatt tttctataca ttttaactat     660
ctatttctgc ataataaact gtattttcat tttatacgct tcatcttatg gatgatattt     720
```

| | | | | |
|---|---|---|---|---|
| aaattttaaa | tagtaattca | tacactttt | aatatttaat | ttagtatttt | cttaaatcca | 780 |
| aattttaatc | ttacaattta | aatatctact | ttaacataat | acaaatacaa | tttaatttca | 840 |
| ttgtattaaa | ttcaaatata | atttgattat | aataaaatac | aatttaattc | taaaaagtcc | 900 |
| atcttagatt | ttaattttcc | ttttttagttt | tgaaaattaa | aaatttaaat | ttattagata | 960 |
| tatatgttac | ttttttcagtt | ttcctattta | tttaagaaaa | aaatattttt | taacacatgt | 1020 |
| caacttgtaa | acaatagact | gaacacgtca | ttttatatta | tgtttagttt | tgaaaattaa | 1080 |
| agttaattaa | atatttatat | ttcttttttt | tagcttttct | aattatttt | aaaatagtaa | 1140 |
| atatttttaa | tacaaatcaa | tatctgaaca | atagatttga | tacataacat | aatcctataa | 1200 |
| attattaact | tggaaaacga | tagtttatat | aataaaatta | ttttcttaag | ttctctaacc | 1260 |
| ataacaatta | aactatattt | tagcgaagaa | aagaagagaa | taccgagaga | acgcaacttg | 1320 |
| cactaaaagc | taccactttg | gcaaatcact | catttatatt | attatatact | atcacctcaa | 1380 |
| ttcaatcgaa | acctcaaaat | aacactaata | tatacacaaa | gaaacaacag | aataacaccg | 1440 |
| aagaatatag | gtttaggaaa | atccagaatt | tgttgagact | aaagagatca | aattttcgat | 1500 |
| acaaggtttt | gctcaatttg | tattttcata | ataaaattct | ttatttcacc | atagacttac | 1560 |
| atgattagtt | tttcttttaa | taaaaaaaaa | cacgcgacat | gaaaattata | ttatctcagt | 1620 |
| gttgtcgaat | ttgaatttga | attttgagtt | aaatactaca | catttgttga | caacttatta | 1680 |
| aactttacaa | gtctgctaca | aatattgtca | aatatttact | aattaatgga | ccaaaatcct | 1740 |
| ctaacttgca | aatttgtatc | tacatcaact | taaaaattag | gaatatgcga | cccaaaaaaa | 1800 |
| aaaaaactag | gaataataat | aaaaaaatgg | aatgatgtgg | aggaagctct | ttactctttg | 1860 |
| agaggaagtt | tataaattga | ccacacattt | agtctattat | catcacatgt | attaagactt | 1920 |
| gacaacttgt | ctttctcaca | ccaaacccct | ctcctctgtt | tcataacatc | tgctctttct | 1980 |
| ttttttttcct | aagcccta | | | | | 1999 |

<210> SEQ ID NO 58
<211> LENGTH: 609
<212> TYPE: DNA
<213> ORGANISM: Glycine max
<220> FEATURE:
<221> NAME/KEY: promoter
<222> LOCATION: (1)..(609)

<400> SEQUENCE: 58

| | | | | | | |
|---|---|---|---|---|---|---|
| gaagccacgt | catgaagagt | atatcatttc | agtaatgttt | tgagacgcct | ctataatgct | 60 |
| ttaccaacaa | aacaaaacaa | aaaaagaac | atttgaaacc | atttgtatta | aaaaaaaaaa | 120 |
| ggtatattag | gccataatat | tataggtaac | atgaaatatc | aaatgacacg | caagagtttt | 180 |
| gtcaaaaatg | aaaccatcac | acatcagaga | ttatggcaaa | taatgttttg | tgtgtctctt | 240 |
| gcttcaccca | taacataagc | ctctataact | ggagagaaga | aaaaaaaaag | tggaggggct | 300 |
| agggtgggaa | tttggaagaa | tacagttata | ttgagcattg | agcaagttga | tagaaagctt | 360 |
| ctcaatttgt | acaaaatttg | catccacatg | attattaaag | acgtagacag | cacttcttcc | 420 |
| ttcttttttt | ctataagttt | cttatatatt | gttcttcatg | ttttaatatt | attacttat | 480 |
| gtacgcgtct | aacagtagtc | ctcccaaact | gctataaata | gagcctcttc | aacgcacctc | 540 |
| ttggcagtac | aaaaattatt | catctcttct | aagttctaat | tttctaagca | ttcagtaaaa | 600 |
| gaactaacc | | | | | | 609 |

<210> SEQ ID NO 59
<211> LENGTH: 1476

```
<212> TYPE: DNA
<213> ORGANISM: Arabidopsis thaliana
<220> FEATURE:
<221> NAME/KEY: promoter
<222> LOCATION: (1)..(1476)

<400> SEQUENCE: 59
gctcgcgtta gttccactca aggagtatcc tttcttcctt gcgcaactct ccaccttcgg      60
gtaaagtacc atctctagca tcttgagtct tgatcaactt ctgttttgct tactctcaaa     120
atgcattaat ttttttttat actagatcat agtattatat ctcttaatct acctattgaa     180
atctacttaa tgttttact aaaacctacg tgtttctctt tagagaattt tgtgctatgc      240
atgaattaga ggttagtaat gtgtaatact tcataagtct agatttattt gttggttaac     300
acgtttagta attcacacac acacaccacc ttagatattt tactgtgaat tagaaaaaga     360
tacatagtta ggagtgtttt tttaaaaaaa ttcaatcatg agaaaattag aggtgtgatg     420
ttatacatta tgaaaatgca aagggcagat acgaataaat tagaaacttg tttaacgggt     480
cagagttggc ttctagtctc tttcgacttg gatacttctt cttctacaat tgggacatta     540
ttgtaggcgc attatatcat ttctctacat gcaatgaatg tacatacatt aattcacatt     600
tattttgga ataatcatat gagtgatcga agtttgtatt tatatattca atcttcacaa      660
actacttta tttaaaaatc atttgcaaaa tgctatttta ttgacaaaaa gatatatgct       720
ataaaataaa ataaaattca caactatag tcattaatac aaaaagaaat cattgaatat      780
ggtagagggg aaacaaaaaa aaaacacgac gatgtaagtt ggtggaacca cattatcaaa     840
ataaaagaag gtggtggaac caaattgaat aaagtccgtc catatcatta tccgtcccctt    900
aggagcctct aattagtaat attcttatgg gtccactgtg gcttagagga cttgattaaa     960
accattctta tttagtgcta actttgtgag ggttggaata acgaaccaag ctgattcaaa    1020
ccattccaaa acaaagttgt cacatatttc aaaaccaaag tttaccggac agagaaatat    1080
ggtgtgtttt tctcaaacca agctaaatgg aatccattgt aaaccaaaat gttcacacct    1140
acctattctt ttggagtccc ttttccatgt gtttgctgtc tgctagtcaa gtttcattag    1200
ctgattgcct tgcatcatat tcttggatca acttttttt tttttttttt tggggtaatt    1260
aacaaaatgc ttaaatttct caagactata ggatcacatt acctgtgtgc ttaacataac    1320
ttttagatag gctagagaat tgatctatta caagataatc ataatttac agaagaaaac     1380
attctttttt ttgttctatt tccttcatgt aggtatgtag ctgtatatta tactatcttg    1440
tattttcgat atcgtgctgg aactgtcaca gatgca                              1476

<210> SEQ ID NO 60
<211> LENGTH: 325
<212> TYPE: DNA
<213> ORGANISM: Petroselinum crispum

<400> SEQUENCE: 60
aattcgaatc caaaaattac ggatatgaat ataggcatat ccgtatccga attatccgtt      60
tgacagctag caacgattgt acaattgctt ctttaaaaaa ggaagaaaga aagaaagaaa     120
agaatcaaca tcagcgttaa caaacggccc cgttacggcc caaacggtca tatagagtaa     180
cggcgttaag cgttgaaaga ctcctatcga aatacgtaac cgcaaacgtg tcatagtcag     240
atcccctctt ccttcaccgc ctcaaacaca aaaataatct tctacagcct atatatacaa     300
cccccccttc tatctctcct ttctc                                           325
```